United States Patent
Kato et al.

(10) Patent No.: US 6,858,380 B2
(45) Date of Patent: Feb. 22, 2005

(54) SILVER HALIDE COLOR PHOTOSENSITIVE MATERIAL

(75) Inventors: Yasuhiro Kato, Minami-Ashigara (JP); Hisashi Mikoshiba, Minami-Ashigara (JP); Naoto Matsuda, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/352,035

(22) Filed: Jan. 28, 2003

(65) Prior Publication Data

US 2003/0203327 A1 Oct. 30, 2003

(30) Foreign Application Priority Data

Jan. 30, 2002 (JP) ......................................... 2002-022349

(51) Int. Cl.$^7$ .............................. G03C 1/08; G03C 7/26; G03C 7/32
(52) U.S. Cl. ...................... 430/558; 430/543; 430/384; 430/385
(58) Field of Search ................................ 430/558, 543, 430/384, 385

(56) References Cited

U.S. PATENT DOCUMENTS

| | | | |
|---|---|---|---|
| 6,159,671 A | * 12/2000 | Matsuda | 430/558 |
| 6,322,959 B1 | * 11/2001 | Matsuda | 430/558 |
| 6,399,291 B1 | 6/2002 | Tateishi et al. | |
| 6,541,192 B2 | * 4/2003 | Kato et al. | 430/558 |
| 2002/0115029 A1 | 8/2002 | Kato et al. | |

FOREIGN PATENT DOCUMENTS

JP 2002-162715 6/2002

* cited by examiner

*Primary Examiner*—Geraldine Letscher
(74) *Attorney, Agent, or Firm*—Sughrue Mion, PLLC

(57) ABSTRACT

A silver halide color photosensitive material comprises at least one layer on a support. At least one of the layers contains a coupler represented by general formula (I):

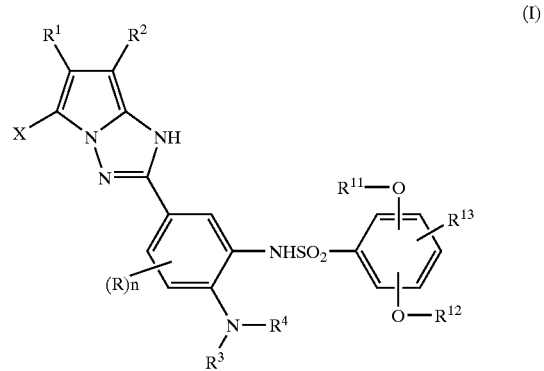

wherein X represents H or split-off group; $R^1$ and $R^2$ independently represents an electron withdrawing group whose Hammett σp value is 0.20 or greater, provided that the sum of $R^1$ and $R^2$ σp values is 0.65 or greater; $R^3$ represents a group selected from alkyl, alkenyl, alkynyl, cycloalkyl, cycloalkenyl, aryl and heterocyclic, each of which may have a substituent; $R^4$ represents H, or a group selected from alkyl, alkenyl, alkynyl, cycloalkyl, cycloalkenyl, aryl, acyl, alkoxycarbonyl, aryloxycarbonyl and carbamoyl, each of which may have a substituent, provided that $R^3$ and $R^4$ may be bonded to form a ring; $R^{11}$, $R^{12}$ and $R^{13}$ independently represent an alkyl group having 1–30 carbon atoms; R represents a substituent; and n represents an integer of 0–3.

8 Claims, No Drawings

SILVER HALIDE COLOR PHOTOSENSITIVE MATERIAL

CROSS-REFERENCE TO RELATED APPLICATIONS

This application is based upon and claims the benefit of priority from the prior Japanese Patent Application No. 2002-22349, filed Jan. 30, 2002, the entire contents of which are incorporated herein by reference.

BACKGROUND OF THE INVENTION

1. Field of the Invention

The present invention relates to a pyrrolotriazole compound having a specific structure, and relates to a silver halide color photosensitive material having its color reproduction and color image durability enhanced, having its staining in various forms inhibited and having its processing stability enhanced by the use of a cyan coupler of the pyrrolotriazole compound.

2. Description of the Related Art

With respect to silver halide color photosensitive materials, it is well known that an oxidized aromatic primary amine color developing agent, which uses exposed silver halides as an oxidizer, reacts with a coupler to thereby produce dyes of indophenol, indoaniline, indamine, azomethine, phenoxazine, phenazine, etc. leading to image formation. In this system of photography, use is made of the subtractive color process, and color images are formed by yellow, magenta and cyan dyes.

In the formation of cyan dye images among these, a phenol-type or naphthol-type coupler is commonly employed. However, the dyes formed from these couplers exhibit undesirable absorption in the yellow to magenta region, thereby posing a problem of deterioration of color reproduction. Therefore, it is demanded to resolve this problem.

Especially in recent years, demands on the system in which image information is digitized and subjected to image processing, and thereafter the image information is exposed to a silver halide color photosensitive material, known as the digital photography, are increasing. Particularly in this system, there is a strong demand for a silver halide color photosensitive material of large color reproduction range wherein formed dyes do not exhibit the above undesirable absorption.

On the other hand, high saturation and large color reproduction range are demanded on reversal films. Since the method of emphasizing an interlayer effect has a drawback of, for example, deterioration in processing dependence, it is demanded to realize the high saturation and large color reproduction range by the use of a coupler of excellent hue.

As means for solving this problem, there have been proposed heterocyclic compounds as described in, for example, U.S. Pat. Nos. 4,728,598 and 4,873,183 and EP 0249453A2. However, the couplers described therein have fatal drawbacks such as low coupling activity and poor dye durability.

As a coupler which overcomes these problems, there have been proposed pyrrolotriazole couplers as described in U.S. Pat. No. 5,256,526 and EP 0545300. It has been revealed that these couplers, although being excellent in hue and coupling activity, need further improvement because color photosensitive materials wherein these couplers are employed are not satisfactory in color image durability. Further, the pyrrolotriazole couplers pose such a problem that at bleach-fix processing, the color formation efficiency is lowered by conversion of dyes to leuco compounds (discoloring of some dyes by reduction), the problem known as the blix color fading. Still further, the couplers pose a problem of cyan staining in various forms. Still further, the conventional pyrrolotriazole cyan couplers have a drawback in that when processed with the use of formalin, the photosensitive material containing the couplers suffer magenta staining upon aging.

Moreover, shortening of processing steps and reduction of replenishment rate are demanded on the color reversal films. The inventors have conducted investigations, and as a result it has been found that there is such a problem that the maximum density drop of cyan is inevitably increased when reduction of replenishment rate has been carried out for not only the color developer but also the reversal bath. Furthermore, this problem is often aggravated in the use of hitherto proposed pyrrolotriazole couplers as compared with the use of conventional phenol-type cyan couplers. Solving this matter is strongly demanded.

BRIEF SUMMARY OF THE INVENTION

Therefore, it is an object of the present invention to provide a novel pyrrolotriazole compound of specific structure which is useful as a coupler of silver halide color photosensitive material and which can be a useful intermediate of chemical, medicinal and agricultural-chemical organic compounds (1). It is another object of the present invention to provide a silver halide color photosensitive material which by virtue of the use of the pyrrolotriazole cyan coupler, is excellent in color reproduction and color image durability (2), and which further realizes reduction of cyan stain resulting from reaction with any remaining color developing agents, reduction of blix fading, extreme reduction of magenta stain and enhancement of processing stability (3).

The inventors have conducted extensive studies on the 2-position substituent and split-off groups with respect to pyrrolotriazole-type couplers of excellent hue. As a result, it has been found that the above objects can be attained by a coupler of unknown really novel structure represented by the following general formula. That is, the above objects have been attained by the following means.

(1) A silver halide color photosensitive material comprising at least one layer on a support, wherein at least one of the layers contains a coupler represented by the following general formula (I):

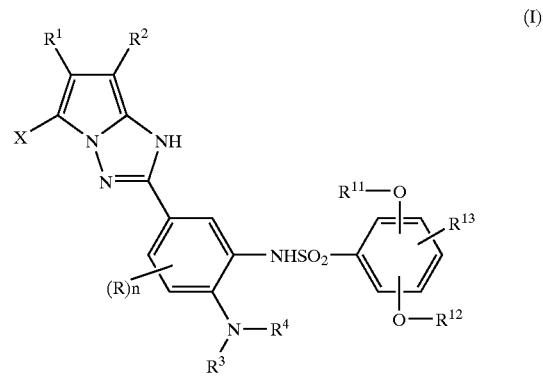

(I)

In the general formula (I), X represents a hydrogen atom or a split-off group; each of $R^1$ and $R^2$ represents an electron withdrawing group whose Hammett substituent constant σp value is 0.20 or greater, provided that the sum of $R^1$ and $R^2$ σp values is 0.65 or greater; $R^3$ represents a substituted or unsubstituted alkyl group, substituted or unsubstituted alkenyl group, substituted or unsubstituted alkynyl group, substituted or unsubstituted cycloalkyl group, substituted or unsubstituted cycloalkenyl group, substituted or unsubstituted aryl group, or substituted or unsubstituted heterocyclic group; $R^4$ represents a hydrogen atom, a substituted or unsubstituted alkyl group, substituted or unsubstituted alkenyl group, substituted or unsubstituted alkynyl group, substituted or unsubstituted cycloalkyl group, substituted or unsubstituted cycloalkenyl group, substituted or unsubstituted aryl group, substituted or unsubstituted acyl group, substituted or unsubstituted alkoxycarbonyl group, substituted or unsubstituted aryloxycarbonyl group, or substituted or unsubstituted carbamoyl group, provided that $R^3$ and $R^4$ may be bonded with each other to thereby form a ring; each of $R^{11}$, $R^{12}$ and $R^{13}$ independently represents a linear, branched or cyclic alkyl group having 1 to 30 carbon atoms; R represents a substituent; and n represents an integer of 0 to 3.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

The present invention will be described in detail below. First, the expression "Hammett substituent constant σp value" used herein will be briefly described. Hammett's rule is a rule of thumb advocated by L. P. Hammett in 1935 for quantitatively considering the effect of substituents on the reaction or equilibrium of benzene derivatives, and the appropriateness thereof is now widely recognized. The substituent constant determined in the Hammett's rule involves σp value and σm value. These values can be found in a multiplicity of general publications, and are detailed in, for example, "Lange's Handbook of Chemistry" 12th edition by J. A. Dean, 1979 (Mc Graw-Hill) and "Kagaku no Ryoiki" special issue, no. 122, p.p. 96 to 103, 1979 (Nankodo). Although in the present invention, substituents are defined by the Hammett substituent constant σp or described thereby, this should not be construed as limitation to only substituents whose values are known by literature and can be found in the above publications, and should naturally be construed as including substituents whose values, even if unknown by literature, would be included in stated ranges when measured according to the Hammett's rule. Further, although the compounds represented by the general formula (I) of the present invention are not benzene derivatives, the σp value is used, irrespective of the position of substitution, as a scale for evaluating the electronic effect of substituents thereof.

In the present invention, the σp value will be used in the above meaning below. The terminology "lipophilicity" used in the present invention refers to a solubility in water at room temperature being 10% or less.

Herein, the heterocycle refers to a ring having a heteroatom therein. The heterocycles include those having aromaticity, and may be condensed with benzene rings, other heterocycles, etc. Further, the heterocycles may have substituents. As the heteroatom, there can be mentioned N, S, O or P. Herein, the substituents and substituents which may be had by the alkyl group, alkenyl group, alkynyl group, cycloalkyl group, cycloalkenyl group, aryl group and heterocycle are not limited as long as they are capable of substituting unless otherwise specified. For example, the substituents can be any of an alkyl group, alkenyl group, alkynyl group, cycloalkyl group, cycloalkenyl group, aryl group, heterocyclic group, acyl group, acyloxy group, acylamino group, alkoxy group, aryloxy group, heterocyclic oxy group, alkoxycarbonyl group, aryloxycarbonyl group, heterocyclic oxycarbonyl group, alkylcarbamoyl group, arylcarbamoyl group, alkylsulfonyl group, arylsulfonyl group, alkylsulfamoyl group, arylsulfamoyl group, alkylsulfonamido group, arylsulfonamido group, alkylamino group, arylamino group, alkylsulfinyl group, arylsulfinyl group, alkylthio group, arylthio group, mercapto group, hydroxyl group, cyano group, nitro group, hydroxylamino group, halogen atom and the like.

The cyan couplers represented by the general formula (I) of the present invention will be described in detail below.

In the general formula (I), X represents a hydrogen atom or a split-off group (namely, a group which can be split off at a coupling reaction with an oxidized color developing agent). The split-off groups represented by X preferably include a halogen atom (a fluorine atom, chlorine atom, bromine atom or iodine atom), alkoxy group having 1 to 32 carbon atoms, aryloxy group having 6 to 32 carbon atoms, alkylthio group having 1 to 32 carbon atoms, arylthio group having 6 to 32 carbon atoms, heterocyclic thio group having 2 to 32 carbon atoms, alkoxycarbonyloxy group having 2 to 32 carbon atoms, aryloxycarbonyloxy group having 7 to 32 carbon atoms, carbamoyloxy group having 1 to 32 carbon atoms, heterocyclic carbonyloxy group having 3 to 32 carbon atoms, 5 or 6-membered nitrogen-containing heterocyclic group having 2 to 32 carbon atoms, the heterocyclic group bonding to the coupling active site with its nitrogen atom, and the like.

The substituent X is preferably a hydrogen atom, halogen atom, arylthio group, carbamoyloxy group or heterocyclic carbonyloxy group. The substituent X is more preferably a hydrogen atom or heterocyclic carbonyloxy group, and most preferably a hydrogen atom.

With respect to the cyan couplers of the present invention, the color formation as cyan images is realized by such a limitation that $R^1$ and $R^2$ both represent electron withdrawing groups of 0.20 or greater σp value, the sum of $R^1$ and $R^2$ Γp values being 0.65 or greater. The sum of $R^1$ and $R^2$ σp values is preferably 0.70 or greater, and the upper limit thereof is about 2.0.

Each of $R^1$ and $R^2$ represents an electron withdrawing group of 0.20 or greater Hammett substituent constant σp value, preferably an electron withdrawing group of 0.30 or greater Hammett substituent constant σp value. The upper limit of the Hammett substituent constant σp value is 1.0 or less.

As examples of $R^1$ and $R^2$ groups which are electron withdrawing groups of 0.20 or greater σp value, there can be mentioned an acyl group, acyloxy group, carbamoyl group, alkoxycarbonyl group, aryloxycarbonyl group, cyano group, nitro group, dialkylphosphono group, diarylphosphono group, diarylphosphinyl group, alkylsulfinyl group, arylsulfinyl group, alkylsulfonyl group, arylsulfonyl group, sulfonyloxy group, acylthio group, sulfamoyl group, thiocyanato group, thiocarbonyl group, halogenated alkyl group, halogenated alkoxy group, halogenated aryloxy group, halogenated alkylamino group, halogenated alkylthio group, aryl group substituted with another electron withdrawing group of 0.20 or greater σp value, heterocyclic group, halogen atom, azo group and selenocyanato group.

The groups capable of further having a substituent among the $R^1$ and $R^2$ groups may further have the following substituents. These substituents can be, for example, a halogen atom, alkyl group, alkenyl group, alkynyl group, cycloalkyl group, cycloalkenyl group, aryl group, heterocyclic group, cyano group, hydroxyl group, nitro group, carboxyl group, sulfo group, amino group, alkoxy group, aryloxy group, acylamino group, alkylamino group, anilino group, ureido group, sulfamoylamino group, alkylthio group, arylthio group, alkoxycarbonylamino group, sulfonamido group, carbamoyl group, sulfamoyl group, sulfonyl group, alkoxycarbonyl group, heterocyclic oxy group, azo group, acyloxy group, carbamoyloxy group, silyloxy group, aryloxycarbonylamino group, imido group, heterocyclic thio group, sulfinyl group, phosphonyl group, aryloxycarbonyl group, acyl group and the like.

More specifically, the substituents of the $R^1$ and $R^2$ groups can be, for example, a halogen atom (e.g., a chlorine atom or bromine atom); alkyl group, alkenyl group, alkynyl group, cycloalkyl group and cycloalkenyl group (e.g., a linear or branched alkyl group having 1 to 32 carbon atoms, aralkyl group having 7 to 38 carbon atoms, linear or branched alkenyl group having 2 to 32 carbon atoms, linear or branched alkynyl group having 2 to 32 carbon atoms, linear or branched cycloalkyl group having 3 to 32 carbon atoms and linear or branched cycloalkenyl group having 3 to 32 carbon atoms, such as methyl, ethyl, propyl, isopropyl, t-butyl, tridecyl, 2-methanesulfonylethyl, 3-(3-pentadecylphenoxy)propyl, 3-{4-{2-[4-(4-hydroxyphenylsulfonyl)phenoxy]dodecanamido}phenyl}propy 1,2-ethoxytridecyl, trifluoromethyl, cyclopentyl, 3-(2,4-di-t-amylphenoxy) propyl, vinyl, 1-propenyl and 2-pentenyl); aryl group (e.g., phenyl, 4-t-butylphenyl, 2,4-di-t-amylphenyl or 4-tetradecanamidophenyl); heterocyclic group (e.g., imidazolyl, pyrazolyl, triazolyl, 2-furyl, 2-thienyl, 2-pyrimidinyl or 2-benzothiazolyl); cyano group, hydroxyl group, nitro group, carboxyl group, sulfo group and amino group; alkoxy group (e.g., methoxy, ethoxy, 2 methoxyethoxy, 2-dodecylethoxy or 2-methanesulfonylethoxy); an aryloxy group (e.g., phenoxy, 2-methylphenoxy, 4-t-butylphenoxy, 3-nitrophenoxy, 3-t-butyloxycarbamoylphenoxy or 3-methoxycarbamoylphenoxy); acylamino group (e.g., acetamido, benzamido, tetradecanamido, 2-(2,4-di-t-amylphenoxy)butanamido, 4-(3-t-butyl-4-hydroxyphenoxy)butanamido or 2-{4-(4-hydroxyphenylsulfonyl)phenoxy}decanamido); alkylamino group (e.g., methylamino, butylamino, dodecylamino, diethylamino or methylbutylamino); anilino group (e.g., phenylamino, 2-chloroanilino, 2-chloro-5-tetradecanaminoanilino, 2-chloro-5-dodecyloxycarbonylanilino, N-acetylanilino or 2-chloro-5-{2-(3-t-butyl-4-hydroxyphenoxy) dodecanamido}anilino); ureido group (e.g., phenylureido, methylureido or N,N-dibutylureido); sulfamoylamino group (e.g., N,N-dipropylsulfamoylamino or N-methyl-N-decylsulfamoylamino); alkylthio group (e.g., methylthio, octylthio, tetradecylthio, 2-phenoxyethylthio, 3-phenoxypropylthio or 3-(4-t-butylphenoxy)propylthio); arylthio group (e.g., phenylthio, 2-butoxy-5-t-octylphenylthio, 3-pentadecylphenylthio, 2-carboxyphenylthio or 4-tetradecanamidophenylthio); alkoxycarbonylamino group (e.g., methoxycarbonylamino or tetradecyloxycarbonylamino); sulfonamido group (e.g., methanesulfonamido, hexadecanesulfonamido, benzenesulfonamido, p-toluenesulfonamido, octadecanesulfonamido or 2-methoxy-5-t-butylbenzenesulfonamido); carbamoyl group (e.g., N-ethylcarbamoyl, N,N-dibutylcarbamoyl, N-(2-dodecyloxyethyl)carbamoyl, N-methyl-N-dodecylcarbamoyl or N-{3-(2,4-di-t-amylphenoxy)propyl}carbamoyl); sulfamoyl group (e.g., N-ethylsulfamoyl, N,N-dipropylsulfamoyl, N-(2-dodecyloxyethyl)sulfamoyl, N-ethyl-N-dodecylsulfamoyl or N,N-diethylsulfamoyl); sulfonyl group (e.g., methanesulfonyl, octanesulfonyl, benzenesulfonyl or toluenesulfonyl); alkoxycarbonyl group (e.g., methoxycarbonyl, butyloxycarbonyl, dodecyloxycarbonyl or octadecyloxycarbonyl); heterocyclic oxy group (e.g., 1-phenyltetrazol-5-oxy or 2-tetrahydropyranyloxy); azo group (e.g., phenylazo, 4-methoxyphenylazo, 4-pivaloylaminophenylazo or 2-hydroxy-4-propanoylphenylazo); acyloxy group (e.g., acetoxy); carbamoyloxy group (e.g., N-methylcarbamoyloxy or N-phenylcarbamoyloxy); silyloxy group (e.g., trimethylsilyloxy or dibutylmethylsilyloxy); aryloxycarbonylamino group (e.g., phenoxycarbonylamino); imido group (e.g., N-succinimido, N-phthalimido or 3-octadecenylsuccinimido); heterocyclic thio group (e.g., 2-benzothiazolylthio or 2,4-diphenoxy-1,3,5-triazole-6-thio or 2-pyridylthio); sulfinyl group (e.g., dodecanesulfinyl, 3-pentadecylphenylsulfinyl or 3-phenoxypropylsulfinyl); phosphonyl group (e.g., phenoxyphosphonyl, octyloxyphosphonyl or phenylphosphonyl); aryloxycarbonyl group (e.g., phenoxycarbonyl); acyl group (e.g., acetyl, 3-phenylpropanoyl, benzoyl or 4-dodecyloxybenzoyl); and the like.

The alkyl of a group having alkyl moiety represented by $R^1$ or $R^2$ means a linear or branched alkyl or cycloalkyl. The substituted alkyl groups comprehend an aralkyl, an alkenyl, an alkynyl and a cycloalkenyl.

Accordingly, the alkoxycarbonyl groups comprehend linear or branched alkoxycarbonyl, aralkyloxycarbonyl, alkenyloxycarbonyl, alkynyloxycarbonyl, cycloalkoxycarbonyl and cycloalkenoxycarbonyl groups.

$R^1$ and $R^2$ will be described in greater detail below. As the electron withdrawing group of 0.20 or greater σp value, there can be mentioned an acyl group (e.g., acetyl, 3-phenylpropanoyl, benzoyl or 4-dodecyloxybenzoyl); acyloxy group (e.g., acetoxy); carbamoyl group (e.g., carbamoyl, N-ethylcarbamoyl, N-phenylcarbamoyl, N,N-dibutylcarbamoyl, N-(2-dodecyloxyethyl)carbamoyl, N-(4-n-pentadecanamido)phenylcarbamoyl, N-methyl-N-dodecylcarbamoyl or N-{3-(2,4-di-t-amylphenoxy) propyl}carbamoyl); alkoxycarbonyl group (e.g., methoxycarbonyl, ethoxycarbonyl, isopropyloxycarbonyl, tert-butyloxycarbonyl, isobutyloxycarbonyl, butyloxycarbonyl, dodecyloxycarbonyl, octadecyloxycarbonyl, cyclohexyloxycarbonyl or cyclohexenoxycarbonyl); aryloxycarbonyl group (e.g., phenoxycarbonyl); cyano group; nitro group; dialkylphosphono group (e.g., dimethylphosphono); diarylphosphono group (e.g., diphenylphosphono); diarylphosphinyl group (e.g., diphenylphosphinyl); alkylsulfinyl group (e.g., 3-phenoxypropylsulfinyl); arylsulfinyl group (e.g., 3-pentadecylphenylsulfinyl); alkylsulfonyl group (e.g., methanesulfonyl or octanesulfonyl); arylsulfonyl group (e.g., benzenesulfonyl or toluenesulfonyl); sulfonyloxy group (e.g., methanesulfonyloxy or toluenesulfonyloxy); acylthio group (e.g., acetylthio or benzoylthio); sulfamoyl group (e.g., N-ethylsulfamoyl, N,N-dipropylsulfamoyl, N-(2-dodecyloxyethyl)sulfamoyl, N-ethyl-N- dodecylsulfamoyl or N,N-diethylsulfamoyl); thiocyanato group; thiocarbonyl group (e.g., methylthiocarbonyl or phenylthiocarbonyl); halogenated alkyl group (e.g., trifluoromethane or heptafluoropropane); halogenated alkoxy group (e.g., trifluoromethyloxy); halogenated aryloxy group (e.g., pentafluorophenyloxy); halogenated alkylamino group (e.g., N,N-di(trifluoromethyl)amino); halogenated alkylthio group (e.g., difluoromethylthio or 1,1,2,2-tetrafluoroethylthio); aryl group substituted with another electron withdrawing group of 0.20 or greater σp value (e.g., 2,4-dinitrophenyl, 2,4,6-trichlorophenyl or pentachlorophenyl); heterocyclic group (e.g., 2-benzoxazolyl, 2-benzothiazolyl, 1-phenyl-2-benzimidazolyl, 5-chloro-1-tetrazolyl or 1-pyrrolyl); halogen atom (e.g., chlorine atom or bromine atom); azo group (e.g., phenylazo); or selenocyanato group.

The groups capable of further having a substituent among these substituents may further have the above substituents.

As preferred examples of $R^1$ and $R^2$ groups, there can be mentioned an acyl group having 2 to 32 carbon atoms, acyloxy group having 2 to 32 carbon atoms, carbamoyl group having 1 to 32 carbon atoms, alkoxycarbonyl group having 2 to 32 carbon atoms, aryloxycarbonyl group having 7 to 32 carbon atoms, cyano group, a nitro group, alkylsulfinyl group having 1 to 32 carbon atoms, arylsulfinyl group having 6 to 32 carbon atoms, alkylsulfonyl group having 1 to 32 carbon atoms, arylsulfonyl group having 6 to 32 carbon atoms, sulfamoyl group having 0 to 32 carbon atoms, halogenated alkyl group having 1 to 32 carbon atoms, halogenated alkoxy group having 1 to 32 carbon atoms, halogenated alkylthio group having 1 to 32 carbon atoms, halogenated aryloxy group having 7 to 32 carbon atoms, aryl group having 7 to 32 carbon atoms substituted with two or more other electron withdrawing groups of 0.20 or greater σp value, and 5 to 8-membered heterocyclic group having 1 to 36 carbon atoms wherein a nitrogen atom, oxygen atom or sulfur atom is contained.

As more preferred examples of $R^1$ and $R^2$ groups, there can be mentioned an alkoxycarbonyl group having 2 to 32 carbon atoms, nitro group, cyano group, arylsulfonyl group having 6 to 32 carbon atoms, carbamoyl group having 1 to 32 carbon atoms and halogenated alkyl group having 1 to 32 carbon atoms. $R^1$ most preferably represents a cyano group. $R^2$ especially preferably represents an alkoxycarbonyl group having 2 to 32 carbon atoms, and most preferably represents a branched alkoxycarbonyl group having 4 to 32 carbon atoms (in particular, cycloalkoxycarbonyl group).

In the general formula (I), $R^3$ represents a substituted or unsubstituted alkyl group, substituted or unsubstituted alkenyl group, substituted or unsubstituted alkynyl group, substituted or unsubstituted cycloalkyl group, substituted or unsubstituted cycloalkenyl group, substituted or unsubstituted aryl group, or substituted or unsubstituted heterocyclic group.

More specifically, the alkyl, alkenyl, alkynyl, cycloalkyl and cycloalkenyl groups represented by $R^3$ can be a linear or branched alkyl group having 1 to 32 carbon atoms, aralkyl group having 7 to 32 carbon atoms, alkenyl group having 2 to 32 carbon atoms, alkynyl group having 2 to 32 carbon atoms, cycloalkyl group having 3 to 32 carbon atoms and cycloalkenyl group having 3 to 32 carbon atoms. Still more specifically, they can be, for example, methyl, ethyl, propyl, isopropyl, t-butyl, tridecyl, 2-methanesulfonylethyl, 3-(3-pentadecylphenoxy)propyl, 3-{4-{2-[4-(4-hydroxyphenylsulfonyl)phenoxy]dodecanamido}phenyl}propy1, 2-ethoxytridecyl, trifluoromethyl, cyclopentyl, 3-(2,4-di-t-amylphenoxy)propyl, vinyl, 1-propenyl and 2-pentenyl. With respect to the aryl group, one having 6 to 36 carbon atoms is preferred, and monocyclic one is more preferred. The aryl group can be, for example, phenyl, 4-t-butylphenyl, 2-methylphenyl, 2,4,6-trimethylphenyl, 2-methoxyphenyl, 4-methoxyphenyl, 2,6-dichlorophenyl, 2-chlorophenyl, 2,4-dichlorophenyl or the like. With respect to the heterocyclic group, a 5 to 8-membered heterocycle having 1 to 36 carbon atoms wherein a nitrogen atom, oxygen atom or sulfur atom is contained is preferred. A 5 or 6-membered heterocycle bonding to —$NR^4$ of the general formula (I) through the nitrogen atom contained in the heterocycle is more preferred. Such a heterocycle may form a condensed ring in cooperation with a benzene ring or another heterocycle. The heterocyclic group can be, for example, any of imidazolyl, pyrazolyl, triazolyl, piperidino, pyrrolidyl, pyrrolyl, morpholino, pyrazolidyl, thiazolidyl and the like, among which pyrrolidyl is preferred.

The groups capable of further having a substituent among these substituents may further have the substituents set forth above as examples with respect to $R^1$ and $R^2$.

Preferably, $R^3$ represents a substituted or unsubstituted alkyl group, substituted or unsubstituted alkenyl group, substituted or unsubstituted alkynyl group, substituted or unsubstituted cycloalkyl group, or substituted or unsubstituted cycloalkenyl group.

$R^4$ represents a hydrogen atom, substituted or unsubstituted alkyl group, substituted or unsubstituted alkenyl group, substituted or unsubstituted alkynyl group, substituted or unsubstituted cycloalkyl group, substituted or unsubstituted cycloalkenyl group, substituted or unsubstituted aryl group, substituted or unsubstituted acyl group, substituted or unsubstituted alkoxycarbonyl group, substituted or unsubstituted aryloxycarbonyl group, substituted or unsubstituted carbamoyl group or the like.

More specifically, $R^4$ can be a hydrogen atom, and the alkyl, alkenyl, alkynyl, cycloalkyl and cycloalkenyl groups represented by $R^4$ can be a linear or branched alkyl group having 1 to 32 carbon atoms, aralkyl group having 7 to 32 carbon atoms, alkenyl group having 2 to 32 carbon atoms, alkynyl group having 2 to 32 carbon atoms, cycloalkyl group having 3 to 32 carbon atoms and cycloalkenyl group having 3 to 32 carbon atoms. Still more specifically, they can be, for example, methyl, ethyl, propyl, isopropyl, t-butyl, tridecyl, 2-methanesulfonylethyl, 3-(3-pentadecylphenoxy)propyl, 3-{4-{2-[4-(4-hydroxyphenylsulfonyl)phenoxy]dodecanamido}phenyl}propyl, 2-ethoxytridecyl, trifluoromethyl, cyclopentyl, 3-(2,4-di-t-amylphenoxy)propyl, vinyl group, 1-propenyl group and 2-pentenyl group. With respect to the aryl group, one having 6 to 36 carbon atoms is preferred, and monocyclic one is more preferred. The aryl group can be, for example, phenyl, 4-t-butylphenyl, 2-methylphenyl, 2,4,6-trimethylphenyl, 2-methoxyphenyl, 4-methoxyphenyl, 2,6-dichlorophenyl, 2-chlorophenyl, 2,4-dichlorophenyl or the like. The acyl group is preferably one having 2 to 32 carbon atoms, and can be, for example, acetyl, pivaloyl, octanoyl or benzoyl. Examples of the alkoxycarbonyl, aryloxycarbonyl and carbamoyl groups can be, for example, those described above with respect to groups employed for substitution of $R^1$ and $R^2$.

The groups capable of further having a substituent among these substituents may further have the substituents set forth above as examples with respect to groups employed for substitution of $R^1$ and $R^2$.

Preferably, $R^4$ represents a substituted or unsubstituted alkyl group, substituted or unsubstituted alkenyl group, substituted or unsubstituted alkynyl group, substituted or unsubstituted cycloalkyl group, substituted or unsubstituted cycloalkenyl group, or substituted or unsubstituted aryl group.

$R^3$ and $R^4$ may be bonded with each other to thereby form a 5 or 6-membered heterocycle bonding to the benzene ring of the general formula (I) trough the nitrogen atom of the general formula (I). This heterocyclic group can be, for example, any of imidazolyl, pyrazolyl, triazolyl, piperidyl, piperidino, pyrrolidinyl, pyrrolyl, morpholyl, morpholino, pyrazolidinyl, thiazolidinyl, pyrazolinyl, piperadinyl and the like. These heterocycles may form a condensed ring in cooperation with a benzene ring or another heterocycle.

With respect to $R^3$ and $R^4$, those which form a ring structure are preferred to those which do not form any ring structure. In particular, groups which form a 6-membered heterocycle bonding to the nitrogen atom are preferred, and those which form morpholino, piperadinyl substituted with an acyl group, piperidino or piperidino substituted with a carboxyl group are more preferred.

In the general formula (I), each of $R^{11}$ and $R^{12}$ represents a linear, branched or cyclic alkyl group having 1 to 30 carbon atoms. In particular, an unsubstituted alkyl group is preferred.

As examples of the substituents represented by $R^{11}$ and $R^{12}$ in the general formula (I), there can be mentioned methyl, ethyl, n-propyl, isopropyl, n-butyl, isobutyl, t-butyl, n-pentyl, isopentyl, n-hexyl, cyclohexyl, n-heptyl, n-octyl, t-octyl, n-nonyl, n-decyl, undecyl, dodecyl and the like.

Preferably, each of $R^{11}$ and $R^{12}$ represents methyl, ethyl, n-propyl, isopropyl, n-butyl, isobutyl, t-butyl, n-pentyl, isopentyl, n-hexyl or cyclohexyl.

More preferably, each of $R^{11}$ and $R^{12}$ represents methyl, ethyl, n-propyl, isopropyl or n-butyl group. Most preferably, each of $R^{11}$ and $R^{12}$ represents n-propyl.

In the general formula (I), $R^{13}$ represents a linear, branched or cyclic alkyl group having 1 to 30 carbon atoms.

As examples of the alkyl group represented by $R^{13}$ in the general formula (I), there can be mentioned methyl, ethyl, n-propyl, isopropyl, n-butyl, isobutyl, t-butyl, n-pentyl, isopentyl, n-hexyl, cyclohexyl, n-heptyl, n-octyl, t-octyl, n-nonyl, n-decyl, undecyl, dodecyl and the like. Of these, tertiary alkyl groups are preferred, which are, for example, t-butyl and t-octyl. A t-octyl group is most preferred.

With respect to the substitution positions of substituents $-OR^{11}$, $-OR^{12}$ and $-R^{13}$ in the general formula (I), it is preferred that $-OR^{11}$, $-OR^{12}$ and $-R^{13}$ be located at 2-position, 5-position and 4-position to the group $NHSO_2-$, respectively, or that $-OR^{11}$, $-OR^{12}$ and $-R^{13}$ be located at 2-position, 3-position and 5-position to the group $NHSO_2-$, respectively.

In the general formula (I), R represents a substituent, and n is an integer of 0 to 3.

As examples of substituents represented by R in the general formula (I), there can be mentioned those set forth above with respect to $R^1$.

An alkyl group and alkoxy group can be mentioned as preferred examples of substituents represented by R in the general formula (I).

In the general formula (I), n is most preferably 0.

For constituting the cyan coupler represented by the general formula (I) of the present invention, it is preferred to employ such a combination that X represents a hydrogen atom, halogen atom, arylthio group, carbamoyloxy group or heterocyclic carbonyloxy group; each of $R^1$ and $R^2$ independently represents a group selected from among a cyano group, alkoxycarbonyl group, nitro group, arylsulfonyl group, carbamoyl group and halogenated alkyl group; $R^3$ and $R^4$ are those which form a ring structure; each of $R^{11}$ and $R^{12}$ represents an alkyl group having 6 or less carbon atoms; $R^{13}$ represents a t-butyl group or t-octyl group; and n is 0.

For constituting the cyan coupler represented by the general formula (I), it is more preferred to employ such a combination that X represents a hydrogen atom, halogen atom or heterocyclic carbonyloxy group; $R^1$ represents a cyano group; $R^2$ represents a branched alkoxycarbonyl group; $R^3$ and $R^4$ are those which form a 6-membered ring structure; each of $R^{11}$ and $R^{12}$ represents an alkyl group having 2 to 4 carbon atoms; $R^{13}$ represents a t-butyl group or t-octyl group; and n is 0.

For constituting the cyan coupler represented by the general formula (I), it is most preferred to employ such a combination that X represents a hydrogen atom; $R^1$ represents a cyano group; $R^2$ represents a branched alkoxycarbonyl group; $R^3$ and $R^4$ are those which form a 6-membered ring structure; each of $R^{11}$ and $R^{12}$ represents an n-propyl group; $R^{13}$ represents a t-octyl group; and n is 0.

For causing the cyan coupler of the present invention to be contained in a silver halide photosensitive material, preferably a red-sensitive silver halide emulsion layer, it is preferred that the cyan coupler be a so-called incorporated coupler. For this purpose, it is preferred that the total number of the carbon atoms of $R^{11}$ to $R^{13}$ be 10 or more.

With respect to the cyan couplers and pyrrolotriazole compounds defined in the present invention, specific examples will be shown below, which however in no way limit the scope thereof.

(1)

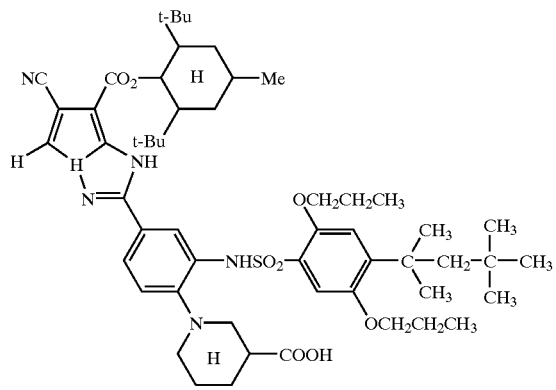

(2)

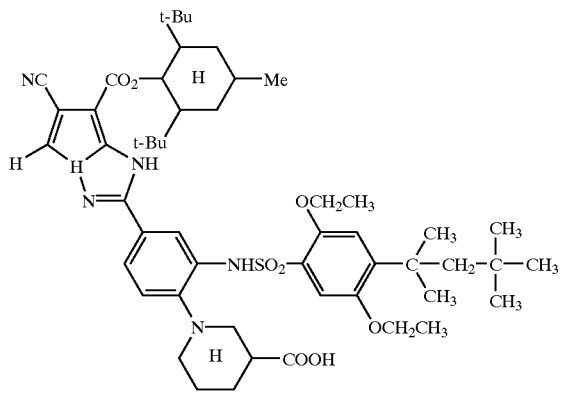

(3)
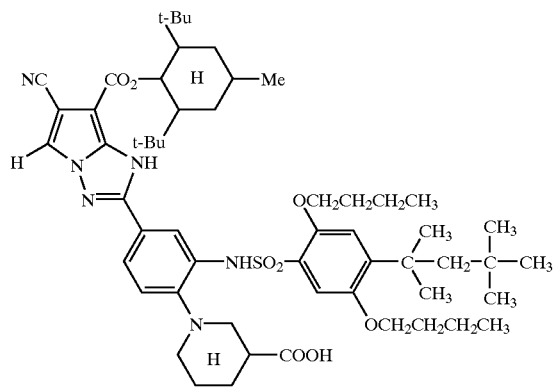
(4)
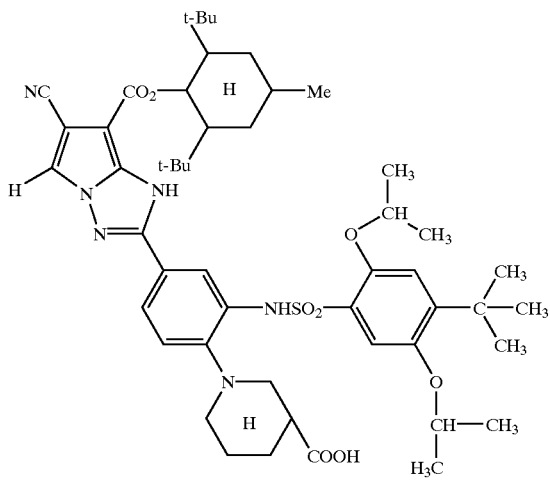
(5)
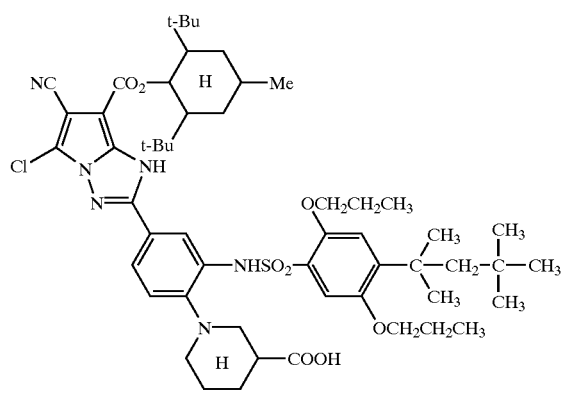
(6)
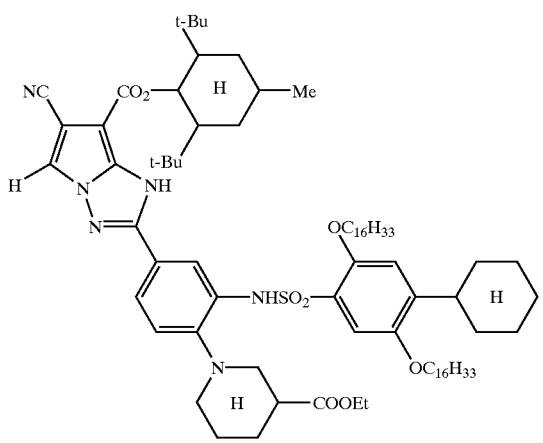
(7)
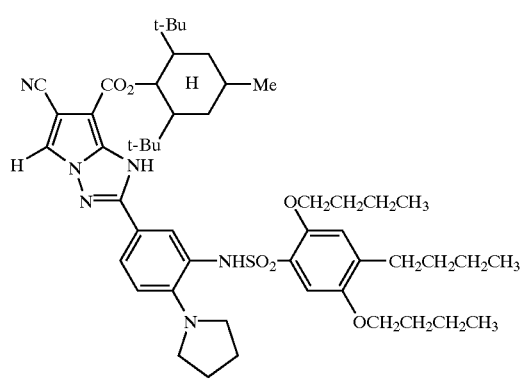
(8)
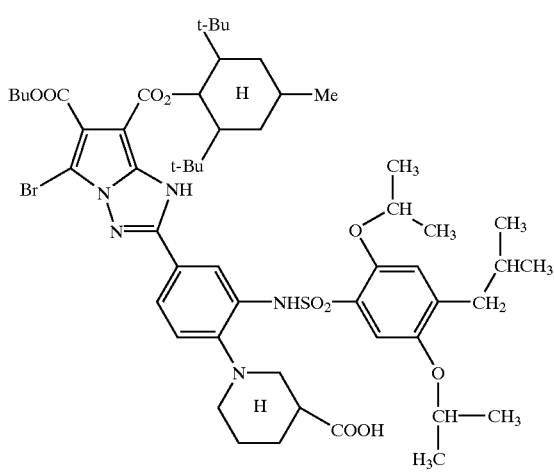

-continued
(9)
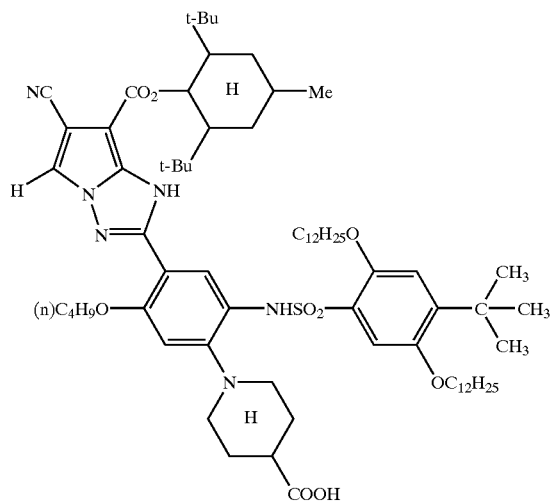
(10)
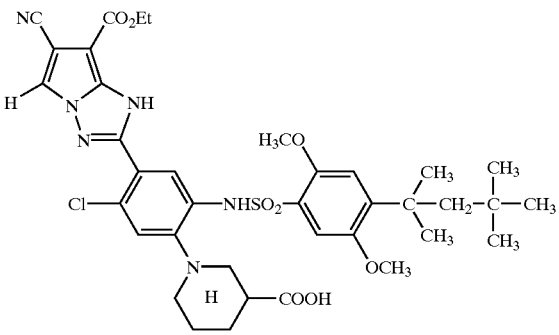
(11)
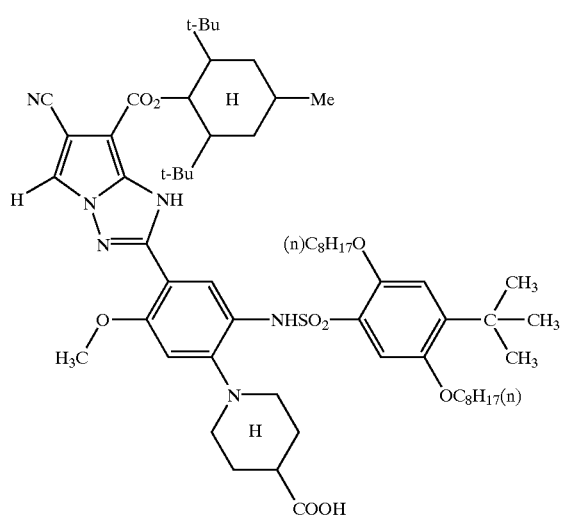
(12)
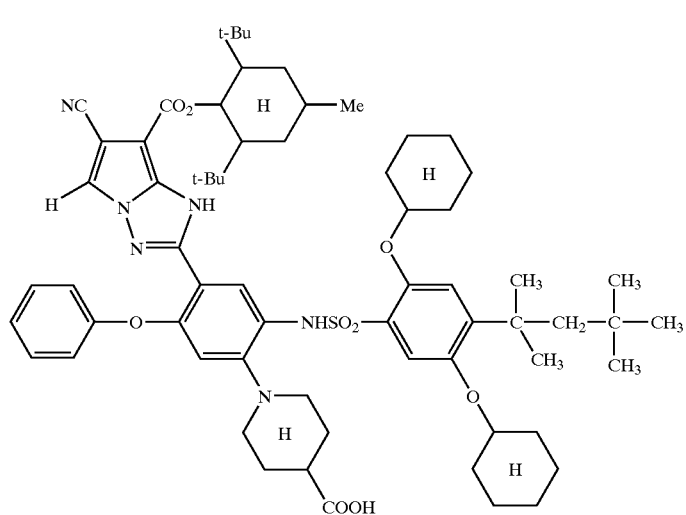

(13)
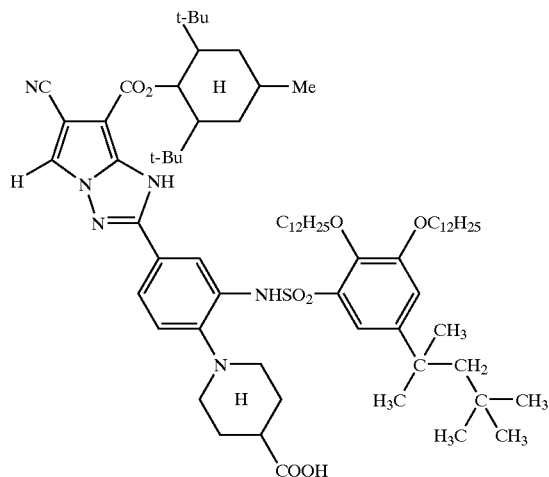
(14)
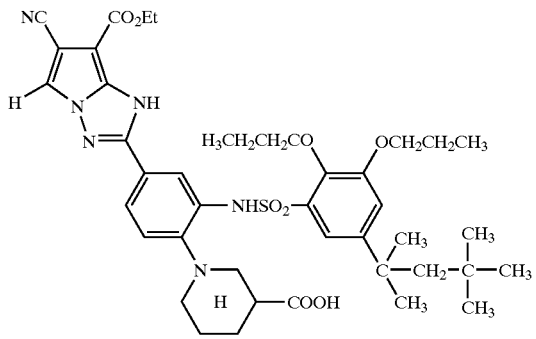
(15)
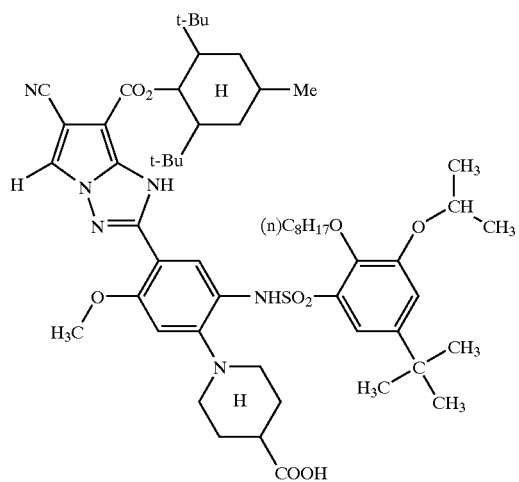
(16)
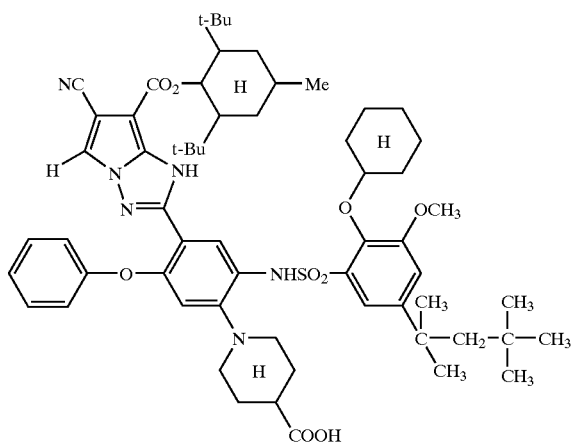
(17)
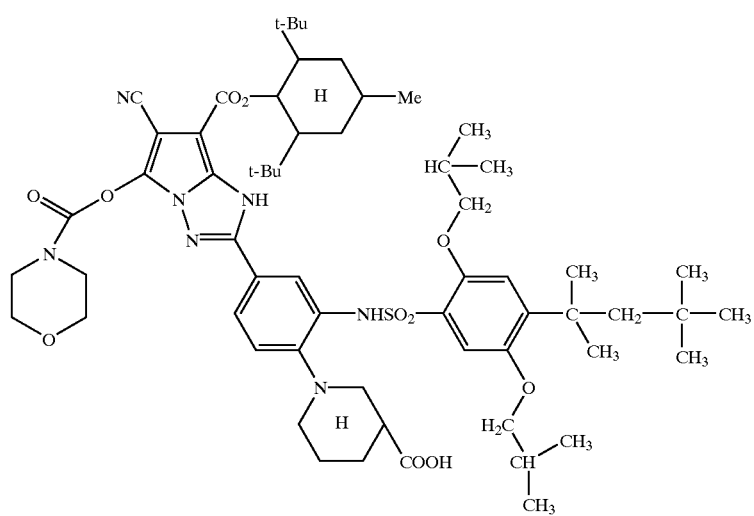

(18)
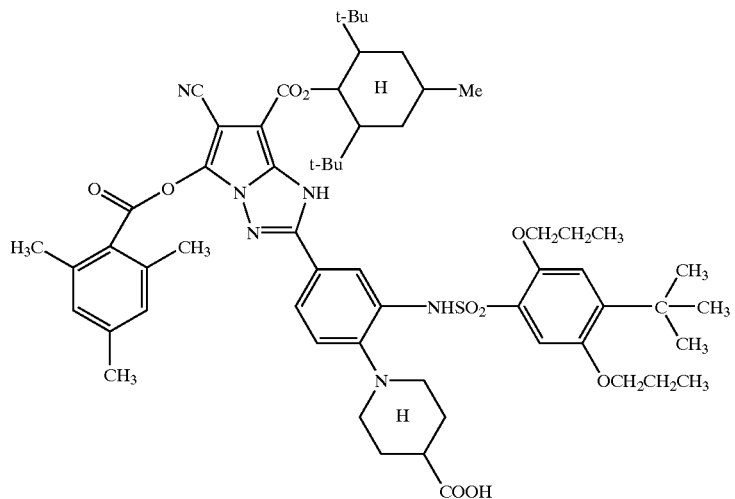
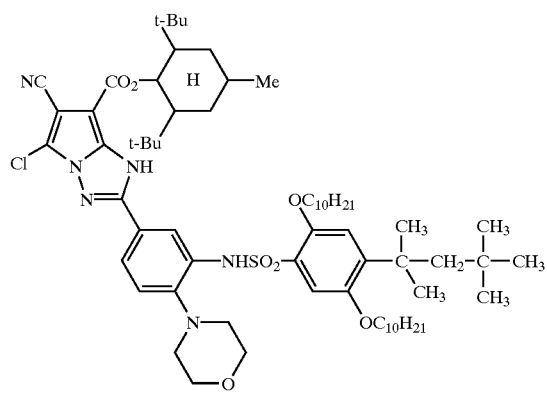
(19)
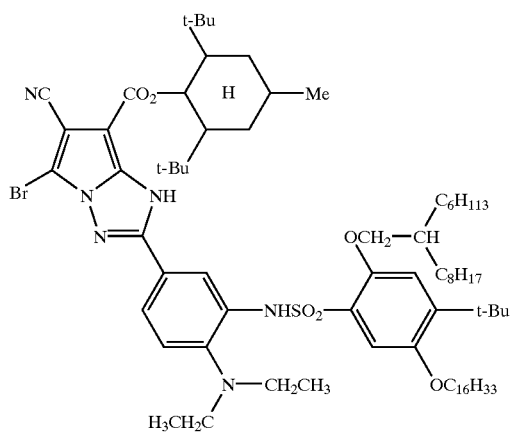
(20)
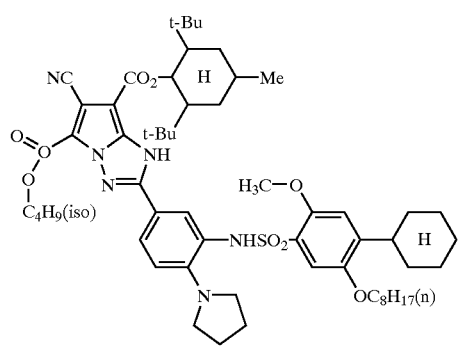
(21)
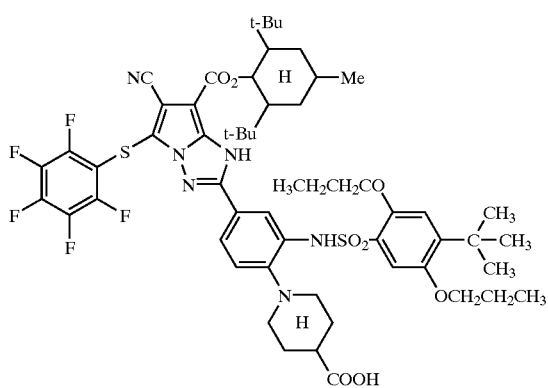
(22)

-continued
(23)
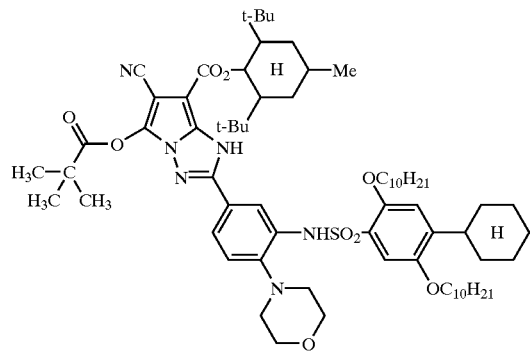
(24)
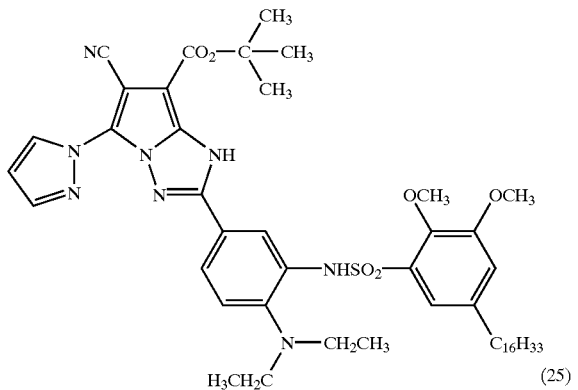
(25)
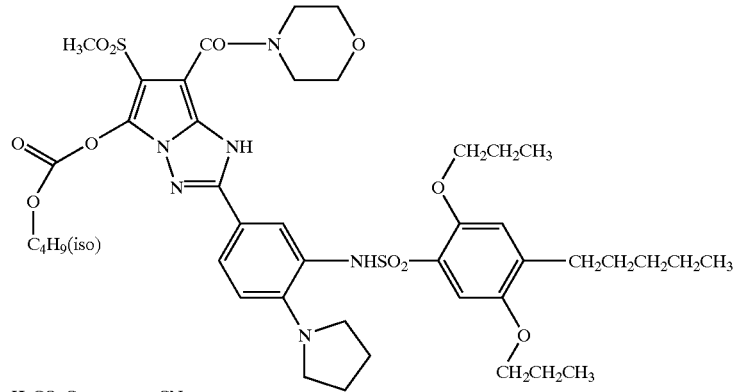
(26)
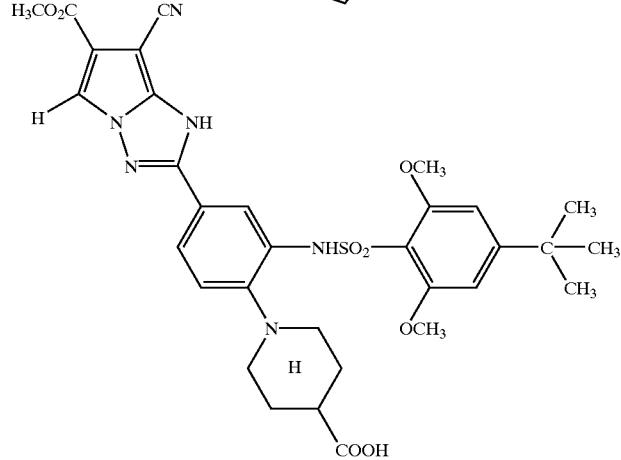
(27)
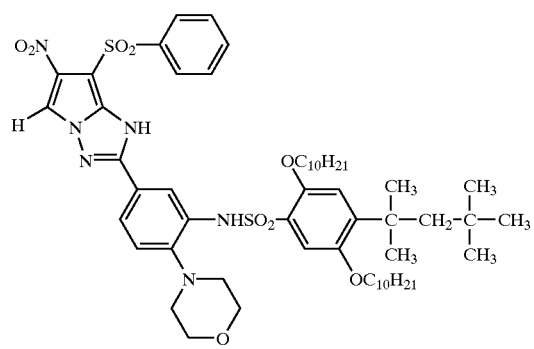
(28)
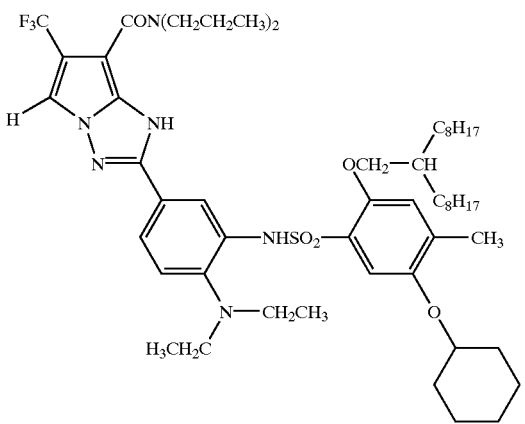

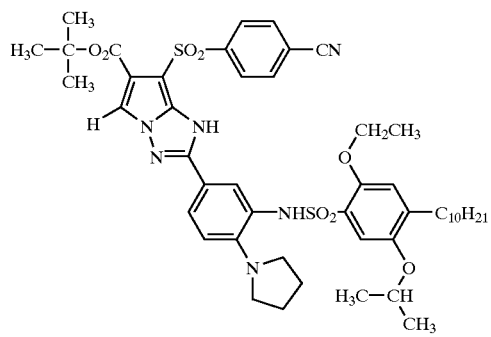
(29)

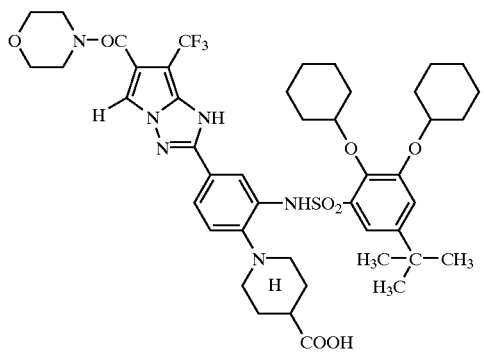
(30)

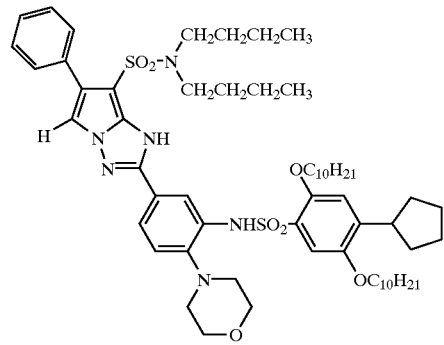
(31)

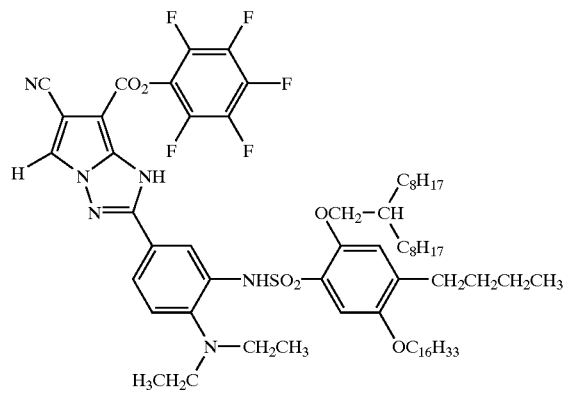
(32)

The compounds of the general formula (I) can be synthesized by the below illustrated processes.

Specific synthetic examples for obtaining pyrrolotriazole compounds according to the present invention will be described below.

Synthetic Example 1 (Synthesis of Exemplified Compound 1)

Exemplified compound (1) was synthesized in accordance with the following synthetic route:

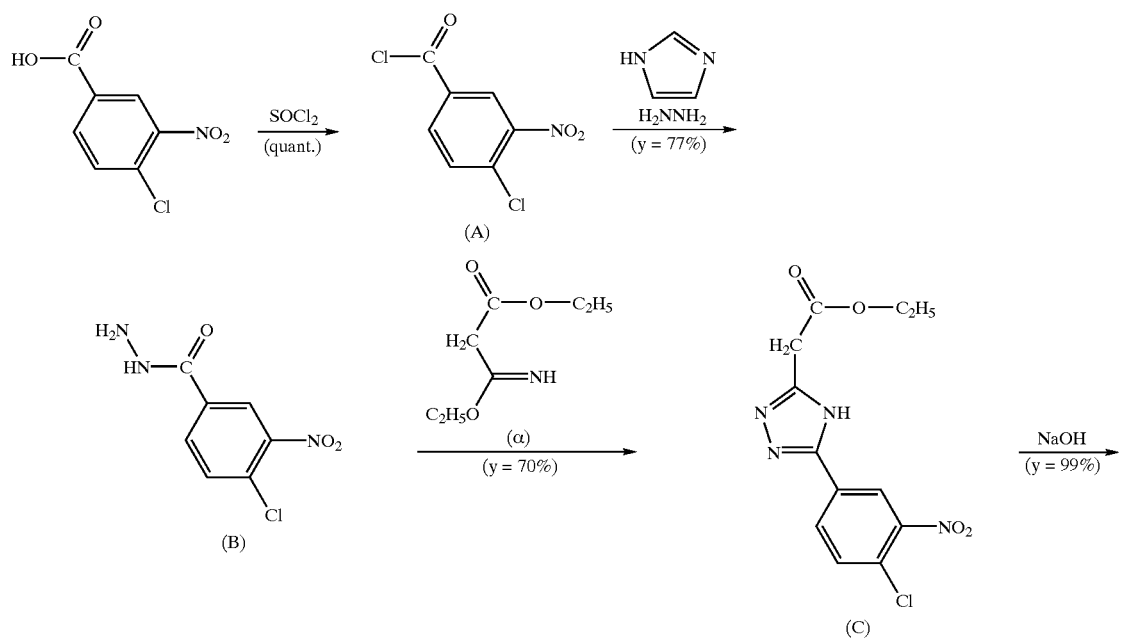

-continued
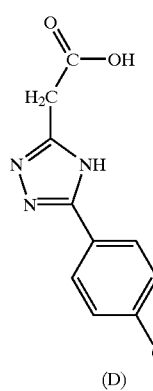 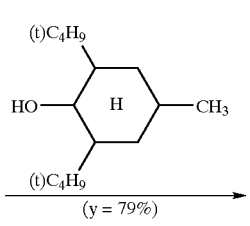 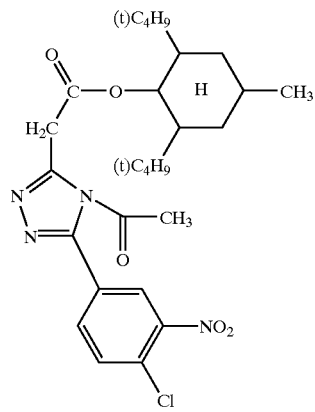 
(D) (E)
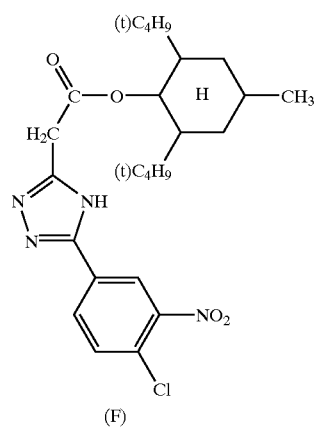 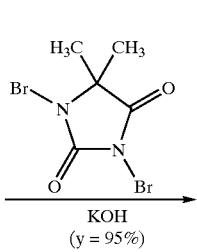 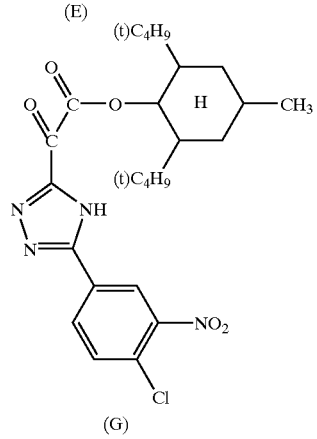 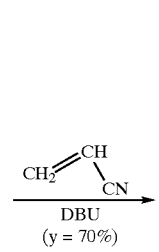
(F) (G)
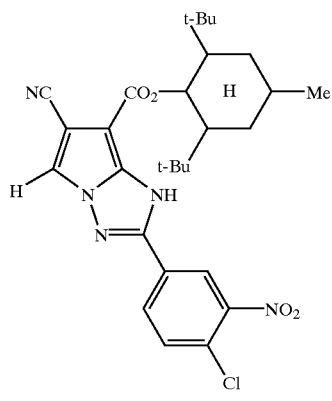 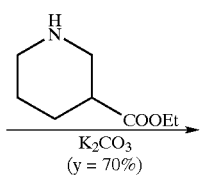
(H)
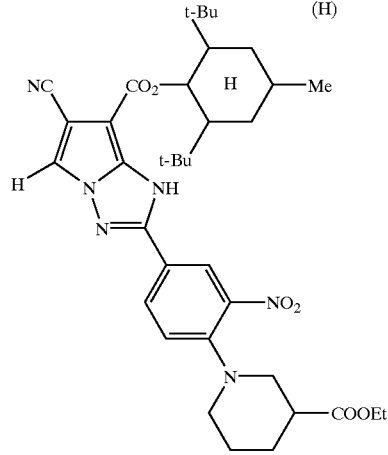 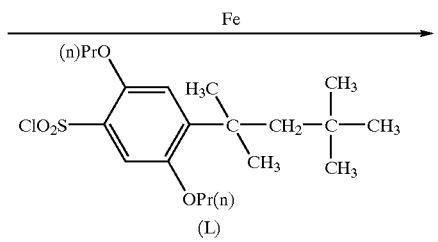
(J) (L)

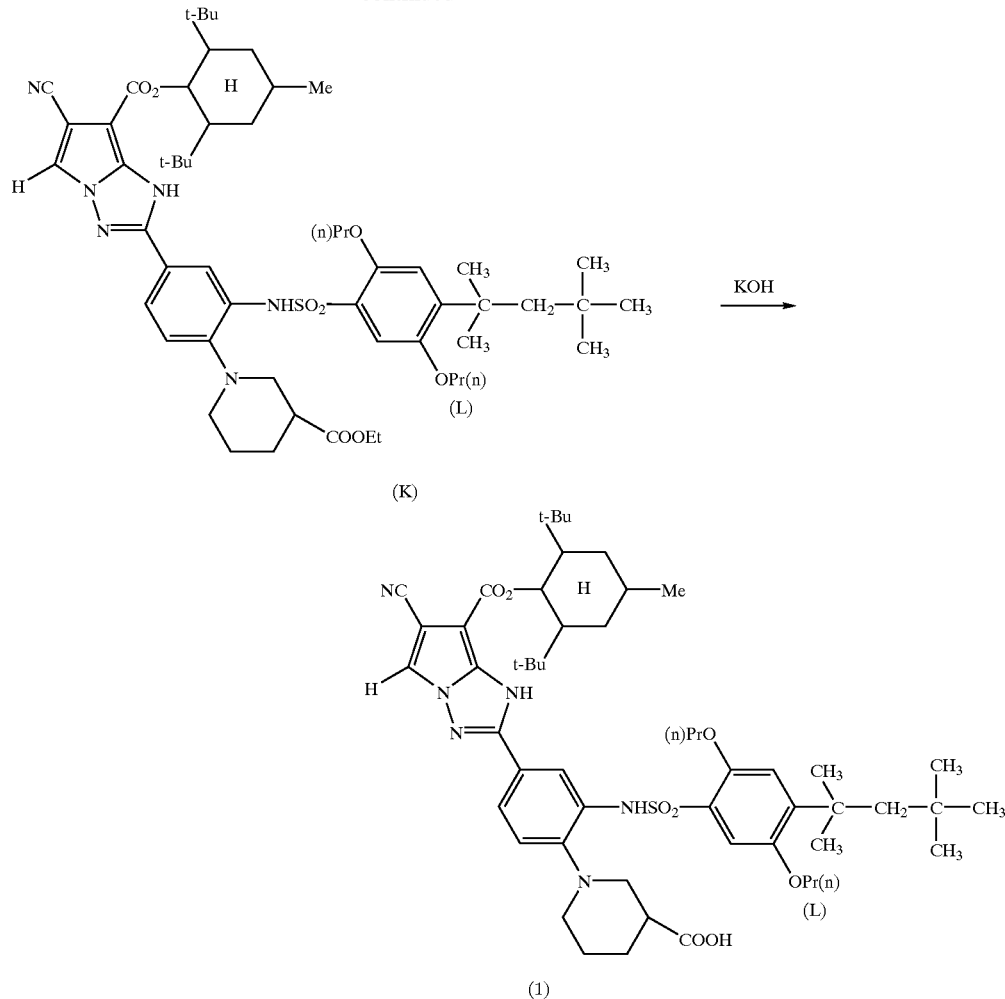

Synthesis of Compound (A):

At 10° C. or below, 76.3 mL (1.05 mol) of thionyl chloride was dropped into a solution obtained by dissolving 202 g (1 mol) of 4-chloro-3-nitrobenzoic acid in 500 milliliters (hereinafter also referred to as "mL") of toluene and 1 mL of N,N-dimethylformamide. The resultant reaction mixture was heated and agitated at reflux temperature for 90 min (the reaction mixture changed from a suspension to a homogeneous liquid). Subsequently, the toluene was distilled off in vacuum. Thus, 220 g of waxy solid (A) was obtained.

Synthesis of Compound (B):

A solution obtained by dissolving 220 g (1 mol) of compound (A) in 300 mL of acetonitrile was slowly dropped into a solution obtained by dissolving 136.2 g (2 mol) of imidazole in 3000 mL of acetonitrile at 5° C. or below. Subsequently, 150 g (3 mol) of hydrazine monohydrate was dropped into the mixture at 13° C. or below. The resultant reaction mixture was agitated at 15° C. for 90 min, and the thus obtained precipitate was harvested by filtration and satisfactorily washed with water. The thus obtained crystal was dried at 5° C. overnight, thereby obtaining 166 g (yield 77%) of compound (B) (melting point: 170–172° C., dec.).

Synthesis of Compound (C):

104.6 mL (0.75 mol) of triethylamine was slowly dropped into a solution obtained by dissolving 146.7 g (0.75 mol) of compound (α-HCl salt) in 500 mL of ethyl acetate at room temperature under agitation, and agitated at room temperature for 30 min. 500 mL of water was added to the mixture, and subjected to liquid separating extraction. An organic layer was separated and washed with a saline solution. The organic layer was dried over magnesium sulfate, and the ethyl acetate was distilled off in vacuum. Thus, 119 g of oily substance (α) was obtained. The obtained 119 g of oily substance (α) was poured into a solution obtained by dissolving 161.7 g (0.75 mol) of compound (B) in 1000 mL of toluene at room temperature under agitation. Subsequently, the reaction mixture was heated, and formed ethanol was distilled off while maintaining the internal temperature thereof at 80° C. Further, the internal temperature was raised to 110° C., distilling off formed water over a period of 3 hr. Thereafter, 500 mL of toluene was distilled off in vacuum, and the internal temperature was lowered to 70–75° C. 500 mL of acetonitrile was slowly poured into the mixture, agitated under reflux for 1 hr, and very slowly cooled until the internal temperature reached room temperature. The mixture was further agitated for 30 min while cooling with water. Separated crystal was harvested by filtration, washed with cold acetonitrile, and dried at 40° C. overnight. Thus, 163 g (yield 70%) of compound (C) (melting point: 152–153° C.) was obtained.

Synthesis of Compound (D):

100 g (2.5 mol) of granular sodium hydroxide was slowly divided and added to a solution obtained by dissolving 155.4 g (0.5 mol) of compound (C) in 1600 mL of methanol under agitation while maintaining the temperature thereof at 10° C. or below by cooling with ice. The resultant reaction mixture was heated to 40° C., and agitated at 40° C. for 90 min. Thereafter, the reaction mixture was cooled to an internal temperature of 30° C., and slowly poured into a solution consisting of 430 mL of hydrochloric acid, 2000 mL of water and 1 kg of crushed ice to thereby effect acid precipitation. Further, the mixture was agitated at 10° C. for 90 min. Crystal was harvested by filtration, washed with water, washed with cold acetonitrile, and dried at 40° C. overnight. Thus, 140 g (yield 99%) of compound (D) (melting point: 133–152° C.) was obtained.

Synthesis of Compound (E):

48.1 g (0.49 mol) of potassium acetate was divided and added to a solution obtained by dissolving 111 g (0.49 mol) of 2,6-di-t-butyl-4-methylcyclohexanol and 138.5 g (0.49 mol) of compound (D) in 1500 mL of ethyl acetate at room temperature under agitation. The thus obtained reaction mixture was cooled to 10° C. or below, and 236 mL (2.5 mol) of acetic anhydride was slowly dropped thereinto while maintaining the internal temperature thereof at 15° C. or below. Subsequently, the reaction mixture was agitated at 40 to 45° C. for 90 min, and the internal temperature thereof was lowered to 5° C. The thus separated crystal was harvested by filtration, satisfactorily washed with water so as to remove any inorganic matter, and finally washed by sprinkling cold acetonitrile. The obtained crystal was dried at 50° C. overnight. Thus, 206.4 g (yield 79%) of compound (E) (melting point: 178–179° C.) was obtained.

Synthesis of Compound (F):

39.2 mL of concentrated hydrochloric acid was slowly dropped into a solution obtained by dissolving 203 g (0.38 mol) of compound (E) in 600 mL of acetonitrile at room temperature. The thus obtained reaction mixture was heated and agitated under reflux for 2 hr. Thereafter, the internal temperature thereof was lowered to 40° C., and 600 mL of water was dropped into the mixture and agitated at room temperature for 1 hr. Separated crystal was harvested by filtration, washed with water, and dried at 50° C. overnight. Thus, 185.1 g (yield 99.2%) of compound (F) (melting point: 191–195° C.) was obtained.

Synthesis of Compound (G):

108.7 g (0.38 mol) of 1,3-dibromo-5,5-dimethylhydantoin was added to a solution obtained by dissolving 181.7 g (0.37 mol) of compound (F) in 700 mL of acetonitrile at room temperature. Subsequently, 0.44 g of methanesulfonic acid was dropped thereinto, and the reaction mixture was heated and agitated under reflux for 90 min. The internal temperature thereof was lowered to 30° C., and 370 mL of N,N-dimethylformamide was poured into the mixture. Further, while cooling with water, a solution obtained by dissolving 45.7 g (0.82 mol) of potassium hydroxide in 150 mL of water was dropped into the mixture at 20 to 25° C. The resultant reaction mixture was agitated at 60° C. for 90 min and cooled to room temperature. 1000 mL of ethyl acetate and 1000 mL of water were added to the mixture to thereby effect extraction. The thus obtained ethyl acetate layer was washed with water and a saline solution, and dried over magnesium sulfate. The solvent was distilled off in vacuum, and recrystallization from acetonitrile was performed. Thus, 178.3 g (yield 95.4%) of compound (G) (melting point: 195–197° C.) was obtained.

Synthesis of Compound (H):

186 g (3.5 mol) of acrylonitrile was poured into a solution obtained by dissolving 176.8 g (0.35 mol) of compound (G) in 370 mL of N,N-dimethylformamide at room temperature. Further, 63.9 g (0.42 mol) of DBU (1,8-diazabicyclo[5.4.0]-7-undecene) was poured thereinto, and the reaction mixture was agitated at 80° C. for 4 hr. The resultant reaction mixture was cooled to room temperature, and 500 mL of acetonitrile was poured thereinto. Further, 72.3 mL of concentrated hydrochloric acid and 1500 mL of water were slowly dropped into the mixture at room temperature. The reaction mixture was agitated at room temperature for 1 hr, and separated crystal was harvested by filtration and washed with water. Crude crystal was subjected to recrystallization from acetonitrile. Thus, 133.3 g (yield 70.5%) of compound (H) (melting point: 265° C., dec.) was obtained.

Synthesis of Compound (J):

A solution obtained by dissolving 77.1 mL (0.5 mol) of ethyl nipecotate and 6.9 g (0.05 mol) of potassium carbonate in 65 mL of N,N-dimethylacetamide was heated under agitation until the internal temperature thereof reached 80° C. A solution obtained by dissolving 27 g of compound (H) in 35 mL of N,N-dimethylacetamide was dropped thereinto, and continued the agitation at 85° C. for 2 hr. The thus obtained reaction mixture was cooled to room temperature, and 150 mL of ethyl acetate and 500 mL of water were added to the mixture to thereby effect extraction. The thus obtained ethyl acetate layer was washed with water and a saline solution, and dried over magnesium sulfate. The solvent was distilled off in vacuum, and recrystallization from acetonitrile was performed. Thus, 25.5 g (yield 77%) of compound (J) (melting point: 178–180° C.) was obtained.

Synthesis of Compound (L):

While nitrogen bubbling, 2,5-di-t-octylhydroquinone (2 kg), propyl tosylate (4.23 kg) and N,N-diethylhydroxylamine (159.4 g) were added to ethanol (6 L). The external temperature was set for 20° C., and when the internal temperature reached 20° C., an aqueous solution of KOH (obtained by dissolving 1.58 kg of KOH in 1.6 liters (hereinafter also referred to as "L") of water) was dropped thereinto while maintaining 40° C. or below. After the completion of dropping, the mixture was agitated at room temperature for 2 hr, and the completion of reaction was ascertained. Water (8 L) was added thereto, and crystal was harvested by filtration. Thus, 2.41 kg of crude crystal of 1,4-dipropoxy-2,5-di-t-octylhydroquinone was obtained. This crude crystal was purified (yield 79.1%) by dispersing the same in acetonitrile (6 L), agitating the dispersion at room temperature for 30 min, cooling the same with ice, agitating the dispersion for more 30 min and effecting filtration thereof. 1.98 kg of thus obtained crystal was dispersed in methylene chloride (5.94 L), and chlorosulfonic acid (630 mL) was dropped into the dispersion at an internal temperature of 11° C. After the completion of dropping, the external temperature was raised to room temperature, and the mixture was agitated for 30 min. After the elimination of raw materials was ascertained, the mixture was again cooled, and N,N-dimethylacetamide (1.98 L) was dropped thereinto at an internal temperature of 12° C. After the completion of dropping, at an internal temperature of 13° C., phosphorus oxychloride (0.88 L) was dropped thereinto. After the completion of dropping, the external temperature was raised to room temperature. The mixture was agitated at room temperature for 30 min, and hexane (9.9 L) was added. Lower layer was removed by liquid separating operation. The hexane layer was washed with a 5% aqueous sodium bicarbonate solution (15 L) and a 5% aqueous hydrochloric acid solution (7.4 L). The external temperature was raised to 60° C., and the solvent, methylene chloride, was distilled off at atmospheric pressure. Acetonitrile (9.9 L) and water (2.48

L) were added to the residue to thereby produce three layers. Lower two layers of the produced three layers were removed by liquid separating operation. Once more, acetonitrile (9.9 L) and water (2.48 L) were added thereto to thereby produce three layers. Lower two layers of the produced three layers were removed by liquid separating operation. The thus obtained organic layer was completely concentrated by means of an evaporator. As a result, oily compound (L) (1.55 kg, 80.9%) was obtained.

Synthesis of Compound (K):

20 g of reduced iron was divided and added to a solution consisting of 2 g of ammonium chloride, 40 mL of water and 200 mL of isopropyl alcohol at room temperature under agitation. Subsequently, the resultant reaction mixture was heated to reflux, and 20 g of compound (J) was slowly divided and added thereto. The mixture was agitated under reflux for 30 min. The thus obtained reaction mixture was subjected to hot Celite filtration, and 100 mL of ethyl acetate and 500 mL of water were added to the filtrate to thereby effect extraction. The ethyl acetate layer was washed with water and a saline solution, and dried over magnesium sulfate. The solvent was distilled off in vacuum, and recrystallization from acetonitrile was performed. Thus, 17.7 g of intermediate ($-NH_2$ derivative) was obtained. Subsequently, 6.5 g (10.32 mmol) of obtained intermediate was divided and added to a solution obtained by dissolving 5.02 g (12.39 mmol) of 2,5-dipropoxy-4-t-octylbenzenesulfonyl chloride (L) in 80 mL of acetonitrile at 50° C. Further, 2 mL of pyridine was dropped thereinto, and agitated under reflux for 1 hr. The reaction mixture was cooled to room temperature, and 150 mL of ethyl acetate and 500 mL of water were added thereto to thereby effect extraction. The ethyl acetate layer was washed with water and a saline solution, and concentrated. Methanol was added to the concentrate, thereby obtaining 8.66 g (yield 89%) of crystal of compound (K) (decomposed at 270° C.)).

(Synthesis of Compound Example 1)

7 mL of methanol, 1.6 mL of water and 0.7 g of potassium hydroxide were added to 1.90 g of compound (K), and agitated for 2 hr while heating at 70° C. After the completion of reaction, the methanol was distilled off in vacuum, and ethyl acetate and water were added to the residue to thereby effect extraction. The thus obtained ethyl acetate layer was washed with water and a 5% aqueous hydrochloric acid solution, and dried over magnesium sulfate. The solvent was distilled off in vacuum, and recrystallization from ethyl acetate/acetonitrile was performed. Thus, 1.59 g (yield 86%) of crystal of compound example (1) was obtained.

The structure of exemplified compound (1) was identified by $^1$H-NMR.

$^1$H-NMR (in $DCDl_3$) of exemplified compound (1): 12.65 (s,1H), 12.0–11.3(bt,1H), 8.17(s,1H), 7.96(s,1H), 7.90(d, 1H), 7.45(s,1H), 7.40(s,1H), 7.26(s,1H), 7.22(d,1H), 6.86(s, 1H), 5.99(s,1H), 4.01–3.95(m,4H), 3.3–3.0(m,3H), 3.0–2.8 (m,1H), 2.60–2.35(m,2H), 2.00–1.5(m,14H), 1.4–1.2(m, 8H), 1.2–1.0(m,9H), 0.92(s,9H), 0.90(s,9H), 0.44(s,9H)

Synthetic Example 2 (Synthesis of Exemplified Compound 2)

Exemplified compound 2 was synthesized in the same manner as in Synthetic Example 1 except that 2,5-diethoxy-4-t-octylbenzenesulfonyl chloride was used in place of 2,5-dipropoxy-4-t-octylbenzenesulfonyl chloride.

Other exemplified compound can also be synthesized in substantially the same manner as in Synthetic Example 1.

The suitable coating amount of cyan coupler according to the present invention is in the range of 0.01 to 2 $g/m^2$, preferably 0.05 to 1.0 $g/m^2$.

The silver halide color photosensitive material of the present invention is only required to have at least one light-sensitive layer on a support. Typical example thereof is a silver halide photosensitive material having at least one light-sensitive unit layer comprising a plural of silver halide emulsion layers each having the substantially the same color sensitivity but different in speed. The light-sensitive unit layer is a unit layer having color sensitivity to any one of blue light, green light and red light. In a multi-layered silver halide color photosensitive material, the arrangement of the unit layer is generally, in the order, from a support, of a red-sensitive layer, green-sensitive layer and blue-sensitive layer. However, the arrangement order may be reversed depending on the purpose of the photographic material. And such an arrangement order that a light-sensitive layer having a different color sensitivity is sandwiched between layers having the same color sensitivity, may be acceptable. A non lightsensitive layer can be formed between the silver halide lightsensitive layers and as the uppermost layer and the lowermost layer. These intermediate layers may contain, e.g., couplers to be described later, DIR compounds and color-mixing inhibitors. As for a plurality of silver halide emulsion layers constituting respective unit lightsensitive layer, a two-layered structure of high- and low-speed emulsion layers can be preferably used in this order so as to the speed becomes lower toward the support as described in DE (German Patent) 1,121,470 or GB 923,045, the entire contents of which are incorporated herein by reference. Also, as described in JP-A's-57-112751, 62-200350, 62-206541 and 62-206543, the entire contents of which are incorporated herein by reference, layers can be arranged such that a low-speed emulsion layer is formed farther from a support and a high-speed layer is formed closer to the support.

More specifically, layers can be arranged from the farthest side from a support in the order of low-speed blue-sensitive layer (BL)/high-speed blue-sensitive layer (BH)/high-speed green-sensitive layer (GH)/low-speed green-sensitive layer (GL)/high-speed red-sensitive layer (RH)/low-speed red-sensitive layer (RL), the order of BH/BL/GL/GH/RH/RL or the order of BH/BL/GH/GL/RL/RH.

In addition, as described in Jpn. Pat. Appln. KOKOKU Publication No. (hereinafter referred to as JP-B-) 55-34932, the entire contents of which are incorporated herein by reference, layers can be arranged from the farthest side from a support in the order of blue-sensitive layer/GH/RH/GL/ RL. Furthermore, as described in JP-A's-56-25738 and 62-63936, the entire contents of which are incorporated herein by reference, layers can be arranged from the farthest side from a support in the order of blue-sensitive layer/GL/ RL/GH/RH.

As described in JP-B-49-15495, the entire contents of which are incorporated herein by reference, three layers can be arranged such that a silver halide emulsion layer having the highest sensitivity is arranged as an upper layer, a silver halide emulsion layer having sensitivity lower than that of the upper layer is arranged as an interlayer, and a silver halide emulsion layer having sensitivity lower than that of the interlayer is arranged as a lower layer; i.e., three layers having different sensitivities can be arranged such that the sensitivity is sequentially decreased toward the support. Even when a layer structure is constituted by three layers having different sensitivities, these layers can be arranged in the order of medium-speed emulsion layer/high-speed emulsion layer/low-speed emulsion layer from the farthest side from a support in a layer sensitive to one color as described in JP-A-59-202464, the entire contents of which are incorporated herein by reference.

In addition, the order of high-speed emulsion layer/low-speed emulsion layer/medium-speed emulsion layer or low-speed emulsion layer/medium-speed emulsion layer/high-speed emulsion layer can be adopted. Furthermore, the arrangement can be changed as described above even when four or more layers are formed.

In order to improve the color reproducibility, a donor layer (CL) of an interlayer effect having a spectral sensitivity distribution different from the main lightsensitive layers BL, GL and RL as described in U.S. Pat. Nos. 4,663,271, 4,705,744 and 4,707,436 and JP-A's-62-160448 and 63-89850, the entire contents of which are incorporated herein by reference, is preferably arranged adjacent to or close to the main lightsensitive layers.

The silver halide preferably used in the present invention is silver iodobromide, silver iodochloride, or silver iodochlorobromide containing about 30 mol % or less of silver iodide. A particularly preferable silver halide is silver iodobromide or silver iodochlorobromide containing about 2 to about 10 mol % of silver iodide.

Silver halide grains contained in the photographic emulsion can have regular crystals such as cubic, octahedral, or tetradecahedral crystals, irregular crystals such as spherical or tabular crystals, crystals having crystal defects such as twin planes, or composite shapes thereof.

The silver halide grain can be a fine grain having a grain size of about 0.2 $\mu$m or less, or be a large grain having a projected area diameter of up to about 10 $\mu$m, and an emulsion can be either a polydisperse or monodisperse emulsion.

A silver halide photographic emulsion which can be used in the present invention can be prepared by methods described in, e.g., Research Disclosure (hereinafter referred to as RD) No. 17643 (December, 1978), pp. 22 and 23, "I. Emulsion preparation and types," RD No. 18716 (November, 1979), page 648, RD No. 307105 (November, 1989), pp. 863 to 865; P. Glafkides, "Chemie et Phisique Photographique", Paul Montel, 1967; G. F. Duffin, "Photographic Emulsion Chemistry", Focal Press, 1966; and V. L. Zelikman et al., "Making and Coating Photographic Emulsion", Focal Press, 1964.

Monodisperse emulsions described in, e.g., U.S. Pat. Nos. 3,574,628 and 3,655,394, and GB1,413,748 are also preferable.

Tabular grains having an aspect ratio of 3 or more can also be used in the present invention. Tabular grains can be easily prepared by methods described in Gutoff, "Photographic Science and Engineering", Vol. 14, pp. 248 to 257 (1970); and U.S. Pat. Nos. 4,434,226, 4,414,310, 4,433,048, and 4,439,520, and GB 2,112,157.

A crystal structure can be uniform, can have different halogen compositions in the interior and the surface layer thereof, or can be a layered structure. Alternatively, a silver halide having a different composition can be bonded by an epitaxial junction or a compound except for a silver halide such as silver rhodamide or lead oxide can be bonded. A mixture of grains having various types of crystal shapes can also be used.

The above emulsion can be any of a surface latent image type emulsion which mainly forms a latent image on the surface of a grain, an internal latent image type emulsion which forms a latent image in the interior of a grain, and another type of emulsion which has latent images on the surface and in the interior of a grain. However, the emulsion must be a negative type emulsion. The internal latent image type emulsion can be a core/shell internal latent image type emulsion described in JP-A-63-264740. A method of preparing this core/shell internal latent image type emulsion is described in JP-A-59-133542. Although the thickness of a shell of this emulsion depends on, e.g., development conditions, it is preferably 3 to 40 nm, and most preferably, 5 to 20 nm.

A silver halide emulsion is normally subjected to physical ripening, chemical ripening, and spectral sensitization steps before it is used. Additives for use in these steps are described in RD Nos. 17643, 18716, and 307105, and they are summarized in a table to be presented later.

In a photosensitive material of the present invention, it is possible to mix, in a single layer, two or more types of emulsions different in at least one of characteristics of a photosensitive silver halide emulsion, i.e., a grain size, grain size distribution, halogen composition, grain shape, and speed.

It is also possible to preferably use surface-fogged silver halide grains described in U.S. Pat. No. 4,082,553, internally fogged silver halide grains described in U.S. Pat. Nos. 4,626,498 and JP-A-59-214852, and colloidal silver, in sensitive silver halide emulsion layers and/or essentially non-sensitive hydrophilic colloid layers. The internally fogged or surface-fogged silver halide grain means a silver halide grain which can be developed uniformly (non-imagewise) regardless of whether the location is a non-exposed portion or an exposed portion of the photosensitive material. A method of preparing the internally fogged or surface-fogged silver halide grain is described in U.S. Pat. Nos. 4,626,498 and JP-A-59-214852. A silver halide which forms the core of an internally fogged core/shell type silver halide grain can have a different halogen composition. As the internally fogged or surface-fogged silver halide, any of silver chloride, silver chlorobromide, silver iodobromide, and silver chloroiodobromide can be used. The equivalent sphere diameter of these fogged silver halide grains is preferably 0.01 to 0.75 $\mu$m, and most preferably, 0.05 to 0.6 $\mu$m. The grain shape can be a regular grain shape. Although the emulsion can be a polydisperse emulsion, it is preferably a monodisperse emulsion (in which at least 95% in weight or number of grains of silver halide grains have equivalent sphere diameters falling within the range of ±40% of the equivalent sphere average diameter).

The equivalent sphere average diameter herein means a volume-weighed average of equivalent sphere diameters of grains. The equivalent sphere diameter means the diameter of a sphere having the same volume as the grain.

In the present invention, it is preferable to use a nonsensitive fine grain silver halide. The non-sensitive fine grain silver halide consists of silver halide grains which are not exposed during imagewise exposure for obtaining a dye image and are not essentially developed during development. These silver halide grains are preferably not fogged in advance. In the fine grain silver halide, the content of silver bromide is 0 to 100 mol %, and silver chloride and/or silver iodide can be added if necessary. The fine grain silver halide preferably contains 0.5 to 10 mol % of silver iodide. The average grain size (the average value of equivalent circle diameters of projected areas) of the fine grain silver halide is preferably 0.01 to 0.5 $\mu$m, and more preferably, 0.02 to 0.2 $\mu$m.

The fine grain silver halide can be prepared following the same procedures as for a common sensitive silver halide. The surface of each silver halide grain need not be optically sensitized nor spectrally sensitized. However, before the silver halide grains are added to a coating solution, it is preferable to add a well-known stabilizer such as a triazole-based compound, azaindene-based compound, benzothiazolium-based compound, mercapto-based compound, or zinc compound. Colloidal silver can be added to this fine grain silver halide grain-containing layer.

The silver coating amount of a photosensitive material of the present invention is preferably 6.0 g/m² or less, most preferably 4.5 g/m².

Photographic additives usable in the present invention are also described in RD's, the entire contents of which are incorporated herein by reference, and the relevant portions are summarized in the following table.

| Types of Additives | RD17643 | RD18716 | RD307105 |
|---|---|---|---|
| 1. Chemical sensitizers | page 23 | page 648 right column | page 866 |
| 2. Sensitivity increasing agents | | page 648 right column | |
| 3. Spectral sensitizers, super sensitizers | pages 23–24 | page 648, right column to page 649, right column | pages 866–868 |
| 4. Brighteners | page 24 | page 647, right column | page 868 |
| 5. Light absorbents, filter dyes, ultraviolet absorbents | pages 25–26 | page 649, right column to page 650, left column | page 873 |
| 6. Binders | page 26 | page 651, left column | pages 873–874 |
| 7. Plasticizers, lubricants | page 27 | page 650, right column | page 876 |
| 8. Coating aids, surfactants | pages 26–27 | page 650, right column | pages 875–876 |
| 9. Antistatic agents | page 27 | page 650, right column | pages 876–877 |
| 10. Matting agents | | | pages 878–879 |

Various dye forming couplers can be used in the photosensitive material of the present invention, and the following couplers are particularly preferable.

Yellow couplers: couplers represented by formulae (I) and (II) in EP No. 502,424A; couplers represented by formulae (1) and (2) in EP No. 513,496A (particularly Y-28 on page 18); a coupler represented by formula (I) in claim 1 of EP No. 568,037A; a coupler represented by general formula (I) in column 1, lines 45 to 55, in U.S. Pat. No. 5,066,576; a coupler represented by general formula (I) in paragraph 0008 of JP-A-4-274425; couplers described in claim 1 on page 40 in EP No. 498,381A1 (particularly D-35 on page 18); couplers represented by formula (Y) on page 4 in EP No. 447,969A1 (particularly Y-1 (page 17) and Y-54 (page 41)); and couplers represented by formulae (II) to (IV) in column 7, lines 36 to 58, in U.S. Pat. No. 4,476,219 (particularly II-17, II-19 (column 17), and II-24 (column 19)), the entire contents of the above documents disclosing the yellow couplers are incorporated herein by reference.

Magenta couplers: JP-A-3-39737 (L-57 (page 11, lower right column), L-68 (page 12, lower right column), and L-77 (page 13, lower right column); [A-4]-63 (page 134), and [A-4]-73 and -75 (page 139) in EP No. 456,257; M-4 and -6 (page 26), and M-7 (page 27) in EP No. 486,965; M-45 (page 19) in EP No. 571,959A; (M–1) (page 6) in JP-A-5-204106; and M-22 in paragraph 0237 of JP-A-4-362631, the entire contents of the above documents disclosing the magenta couplers are incorporated herein by reference.

Cyan couplers: CX-1, CX-3, CX-4, CX-5, CX-11, CX-12, CX-14, and CX-15 (pages 14 to 16) in JP-A-4-204843; C-7 and C-10 (page 35), C-34 and C-35 (page 37), and (I-1) and (I-17) (pages 42 and 43) in JP-A-4-43345; and couplers represented by general formulae (Ia) and (Ib) in claim 1 of JP-A-6-67385, the entire contents of the above documents disclosing the cyan couplers are incorporated herein by reference.

Polymer couplers: P-1 and P-5 (page 11) in JP-A-2-44345, the entire contents of which are incorporated herein by reference.

Couplers for forming a colored dye with a proper diffusibility are preferably those described in U.S. Pat. No. 4,366,237, GB 2,125,570, EP 96,873B, and DE 3,234,533, the entire contents of which are incorporated herein by reference.

As couplers for correcting the unnecessary absorption of a colored dye, preferred use is made of, yellow colored cyan couplers represented by formulae (CI), (CII), (CIII), and (CIV) described on page 5 in EP No. 456,257A1 (particularly YC-86 on page 84); yellow colored magenta couplers ExM-7 (page 202), Ex-1 (page 249), and EX-7 (page 251) described in EP No. 456,257A1; magenta colored cyan couplers CC-9 (column 8) and CC-13 (column 10) described in U.S. Pat. No. 4,833,069; (2) (column 8) in U.S. Pat. No. 4,837,136; and colorless masking couplers represented by formula (A) in claim 1 of WO No. 92/11575 (particularly compound examples on pages 36 to 45), the entire contents of all the documents disclosing the couplers for correcting the unnecessary absorption of a colored dye are incorporated herein by reference.

Examples of couplers that release a photo-graphically useful group are as follows, the entire contents of the patent documents and etc. described below are incorporated herein by reference. Development inhibitor-releasing compounds: compounds represented by formulae (I), (II), (III), and (IV) on page 11 of EP No. 378,236A1 (particularly T-101 (page 30), T-104 (page 31), T-113 (page 36), T-131 (page 45), T-144 (page 51), and T-158 (page 58)); a compound represented by formula (I) on page 7 of EP No. 436,938A2 (particularly D-49 (page 51)); a compound represented by formula (1) in EP No. 568,037A (particularly (23). (page 11)); and compounds represented by formulae (I), (II), and (III) on pages 5 and 6 of EP No. 440,195A2 (particularly I-(1) on page 29). Bleaching accelerator-releasing compounds: compounds represented by formulae (I) and (I') on page 5 of EP No. 310,125A2 (particularly (60) and (61) on page 61); and compounds represented by formula (I) in claim 1 of JP-A-6-59411 (particularly (7) (page 7)). Ligand-releasing compounds: compounds represented by LIG-X described in claim 1 of U.S. Pat. No. 4,555,478 (particularly compounds in column 12, lines 21 to 41). Leuco dye-releasing compounds: compounds 1 to 6 in columns 3 to 8 of U.S. Pat. No. 4,749,641. Fluorescent dye-releasing compounds: compounds represented by COUP-DYE in claim 1 of U.S. Pat. No. 4,774,181 (particularly compounds 1 to 11 in columns 7 to 10). Development accelerator- or fogging agent-releasing compounds: compounds represented by formulae (1), (2), and (3) in column 3 of U.S. Pat. No. 4,656,123 (particularly (I-22) in column 25); and ExZK-2 on page 75, lines 36 to 38, in EP No. 450,637A2. Compounds which release a group which does not function as a dye unless it splits off: compounds represented by formula (I) in claim 1 of U.S. Pat. No. 4,857,447 (particularly Y-1 to Y-19 in columns 25 to 36).

Preferable examples of additives other than couplers are as follows, the entire contents of the patent and other documents described below are incorporated herein by reference:

Dispersion mediums of an oil-soluble organic compound: P-3, P-5, P-16, P-19, P-25, P-30, P-42, P-49, P-54, P-55, P-66, P-81, P-85, P-86, and P-93 (pages 140 to 144) in JP-A-62-215272. Impregnating latexes of an oil-soluble organic compound: latexes described in U.S. Pat. No. 4,199,363. Scavengers of developing agent in an oxidized form: compounds represented by formula (I) in column 2, lines 54 to 62, in U.S. Pat. No. 4,978,606 (particularly I-(1), I-(2), I-(6), and I-(12) (columns 4 and 5)), and formulae in column 2, lines 5 to 10, in U.S. Pat. No. 4,923,787 (particularly compound 1 (column 3)). Stain inhibitors: formulae (I) to (III) on page 4, lines 30 to 33, particularly I-47, I-72, III-1, and III-27 (pages 24 to 48) in EP No. 298321A. Discoloration inhibitors: A-6, A-7, A-20, A-21, A-23, A-24, A-25, A-26, A-30, A-37, A-40, A-42, A-48, A-63, A-90, A-92, A-94, and A-164 (pages 69 to 118) in EP No. 298,321A; II-1 to III-23, particularly III-10, in columns 25 to 38 of U.S. Pat. No. 5,122,444; I-1 to III-4, particularly II-2, on pages 8 to 12 in EP No. 471,347A; and A-1 to A-48, particularly A-39 and A-42, in columns 32 to 40 of U.S. Pat. No. 5,139,931. Materials which reduce the use amount of a color enhancer or a color-mixing inhibitor: I-1 to II-15, particularly I-46, on pages 5 to 24 in EP No. 411,324A. Formalin scavengers: SCV-1 to SCV-28, particularly SCV-8, on pages 24 to 29 in EP No. 477,932A. Film hardeners: H-1, H-4, H-6, H-8, and H-14 on page 17 in JP-A-1-214845; compounds (H-1 to H-54) represented by formulae (VII) to (XII) in columns 13 to 23 of U.S. Pat. No. 4,618,573;, compounds (H-1 to H-76), particularly H-14, represented by formula (6) on page 8, lower right column, in JP-A-2-214852; and compounds described in claim 1 of U.S. Pat. No. 3,325,287. Development inhibitor precursors: P-24, P-37, and P-39 (pages 6 and 7) in JP-A-62-168139; and compounds described in claim 1, particularly 28 and 29 in column 7, of U.S. Pat. No. 5,019,492. Antiseptic agents and mildewproofing agents; I-1 to III-43, particularly II-1, II-9, II-10, II-18, and III-25, in columns 3 to 15 of U.S. Pat. No. 4,923,790. Stabilizers and antifoggants: I-1 to (14), particularly I-1, I-60, (2), and (13), in columns 6 to 16 of U.S. Pat. No. 4,923,793; and compounds 1 to 65, particularly compound 36, in columns 25 to 32 of U.S. Pat. No. 4,952,483. Chemical sensitizers: triphenylphosphine, selenide, and compound 50 in JP-A-5-40324. Dyes: a-1 to b-20, particularly a-1, a-12, a-18, a-27, a-35, a-36, and b-5, on pages 15 to 18 and V-1 to V-23, particularly V-1, on pages 27 to 29 in JP-A-3-156450; F-I-1 to F-II-43, particularly F-I-11 and F-II-8, on pages 33 to 55 in EP No. 445,627A; III-1 to III-36, particularly III-1 and III-3, on pages 17 to 28 in EP No. 457,153A; microcrystalline dispersions of Dye-1 to Dye-124 on pages 8 to 26 in WO No. 88/04794; compounds 1 to 22, particularly compound 1, on pages 6 to 11 in EP No. 319,999A; compounds D-1 to D-87 (pages 3 to 28) represented by formulae (1) to (3) in EP No. 519,306A; compounds 1 to 22 (columns 3 to 10) represented by formula (I) in U.S. Pat. No. 4,268,622; and compounds (1) to (31) (columns 2 to 9) represented by formula (I) in U.S. Pat. No. 4,923,788. UV absorbents: compounds (18b) to (18r) and 101 to 427 (pages 6 to 9) represented by formula (1) in JP-A-46-3335; compounds (3) to (66) (pages 10 to 44) represented by formula (I) and compounds HBT-1 to HBT-10 (page 14) represented by formula (III) in EP No. 520,938A; and compounds (1) to (31) (columns 2 to 9) represented by formula (1) in EP No. 521,823A.

The present invention can be applied to various color photosensitive materials such as color negative films for general purposes or cinemas, color reversal films for slides and TV, color paper, color positive films and color reversal paper. Moreover, the present invention is suitable to lens-equipped film units described in JP-B-2-32615 and Jpn. Utility Model Appln. KOKOKU Publication No. 3-39784.

Supports which can be suitably used in the present invention are described in, e.g., RD. No. 17643, page 28; RD. No. 18716, from the right column of page 647 to the left column of page 648; and RD. No. 307105, page 879.

In the photosensitive material of the present invention, the total of thickness of all the hydrophilic colloidal layers on the side having emulsion layers is preferably 28 $\mu$m or less, more preferably 23 $\mu$m or less, especially preferably 18 $\mu$m or less. The film swelling speed $T_{1/2}$ is preferably 30 sec or less, and more preferably, 20 sec or less. The film swelling speed $T_{1/2}$ is defined as the time that spent for the film thickness to reach 1/2 of the saturation film thickness, wherein the saturation film thickness means 90% of the maximum swollen film thickness realized by the processing in a color developing solution at 30° C. for 3 min 15 sec. The film thickness means one measured under moisture conditioning at 25° C. and at a relative humidity of 55% (two days). The film swelling speed $T_{1/2}$ can be measured by using a swellometer described in A. Green et al., Photogr. Sci. Eng., Vol. 19, No. 2, pp. 124 to 129. The film swelling speed $T_{1/2}$ can be regulated by adding a film hardening agent to gelatin as a binder or by changing aging conditions after coating. The swelling ratio preferably ranges from 150 to 400%. The swelling ratio can be calculated from the maximum swollen film thickness measured under the above conditions in accordance with the formula:

[maximum swollen film thickness–film thickness]/film thickness × 100.

In the photosensitive material of the present invention, hydrophilic colloid layers (called "back layers") having a total dried film thickness of 2 to 20 $\mu$m are preferably formed on the side opposite to the side having emulsion layers. The back layers preferably contain the above light absorbent, filter dye, ultraviolet absorbent, antistatic agent, film hardener, binder, plasticizer, lubricant, coating aid and surfactant. The swelling ratio of the back layers is preferably 150% to 500%.

The photosensitive material of the present invention can be developed by conventional methods described in RD. No. 17643, pages 28 and 29; RD No. 18716, page 651, left to right columns; and RD No. 307105, pages 880 and 881.

The color negative film processing solution for use in the present invention will be described below.

The compounds listed in page 9, right upper column, line 1 to page 11, left lower column, line 4 of JP-A-4-121739 can be used in the color developing solution for use in the present invention. Preferred color developing agents for use in especially rapid processing are 2-methyl-4-[N-ethyl-N-(2-hydroxyethyl)amino]aniline, 2-methyl-4-[N-ethyl-N-(3-hydroxypropyl)amino]aniline and 2-methyl-4-[N-ethyl-N-(4-hydroxybutyl)amino]aniline.

These color developing agents are preferably used in an amount of 0.01 to 0.08 mol, more preferably 0.015 to 0.06 mol, and much more preferably 0.02 to 0.05 mol per liter (L) of the color developing solution. The replenisher of the color developing solution preferably contains the color developing agent in an amount corresponding to 1.1 to 3 times the above concentration, more preferably 1.3 to 2.5 times the above concentration.

Hydroxylamine can widely be used as preservatives of the color developing solution. When enhanced preserving properties are required, it is preferred to use hydroxylamine derivatives having substituents for example, alkyl, hydroxyalkyl, sulfoalkyl and carboxyalkyl groups, examples of which include N,N-di(sulfoethyl)hydroxylamine, monomethylhydroxylamine, dimethylhydroxylamine, monoethylhydroxylamine, diethylhydroxylamine and N,N-di(carboxyethyl)hydroxylamine. Of these, N,N-di(sulfoethyl)hydroxylamine is most preferred. Although these may be used in combination with the hydroxylamine, it is preferred that one or at least two members thereof be used in place of the hydroxylamine.

These preservatives are preferably used in an amount of 0.02 to 0.2 mol, more preferably 0.03 to 0.15 mol, and most preferably 0.04 to 0.1 mol per liter of the color developing solution. The replenisher of the color developing solution preferably contains the preservative in an amount corresponding to 1.1 to 3 times the concentration of the mother liquor (processing tank solution) as in the color developing agent.

Sulfurous salts are used as tarring preventives for the color developing agent in an oxidized form in the color developing solution. Each sulfurous salt is preferably used in the color developing solution in an amount of 0.01 to 0.05 mol, more preferably 0.02 to 0.04 mol per liter, and is preferably used in the replenisher in an amount corresponding to 1.1 to 3 times the above concentration.

The pH value of the color developing solution preferably ranges from 9.8 to 11.0, especially preferably from 10.0 to 10.5. That of the replenisher is preferably set at 0.1 to 1.0 higher than the above value. Common buffers such as carbonate, phosphonate, sulfosalicylate and borate are used for stabilizing the above pH value.

Although the amount of the replenisher of the color developing solution preferably ranges from 80 to 1300 mL per m$^2$ of the photosensitive material, it is desired that the amount be smaller from the viewpoint of reducing environmental pollution load. Specifically, the amount of the replenisher more preferably ranges from 80 to 600 mL, most preferably from 80 to 400 mL.

Although the bromide ion concentration of the color developing solution generally ranges from 0.01 to 0.06 mol per liter, it is preferred that the above concentration be set at 0.015 to 0.03 mol per liter for inhibiting fog while maintaining speed to thereby improve discrimination and for bettering graininess. When the bromide ion concentration is set so as to fall within the above range, the replenisher preferably contains bromide ion in a concentration as calculated by the following formula. However, when C is negative, it is preferred that no bromide ion be contained in the replenisher.

$$C = A - W/V$$

wherein
C: bromide ion concentration of the color developing replenisher (mol/L),
A: target bromide ion concentration of the color developing solution (mol/L),
W: amount of bromide ions which elutes from the photosensitive material to the color developing solution when a 1 m$^2$ of photosensitive material is color-developed (mol),
V: amount of color developing replenisher supplied per m$^2$ of the photosensitive material (L).

Development accelerators such as pyrazolidones represented by 1-phenyl-3-pyrazolidone and 1-phenyl-2-methyl-2-hydroxymethyl-3-pyrazolidone and thioether compounds represented by 3,6-dithia-1,8-octanediol are preferably used as means for enhancing speed when the amount of the replenisher has been reduced or when a high bromide ion concentration has been set.

Compounds and processing conditions described on page 4, left lower column, line 16 to page 7, left lower column, line 6 of JP-A-4-125558 can be applied to the processing solution having bleaching capability for use in the present invention.

Bleaching agents having redox potentials of at least 150 mV are preferably used. Specifically, suitable examples thereof are those described in JP-A-5-72694 and JP-A-5-173312, and especially suitable examples thereof are 1,3-diaminopropanetetraacetic acid and ferric complex salts of Example 1 compounds listed on page 7 of JP-A-5-173312.

For improving the biodegradability of the bleaching agent, it is preferred that ferric complex salts of compounds listed in JP-A's-4-251845, and 4-268552, EP Nos. 588,289, and 591,934 and JP-A-6-208213 be used as the bleaching agent. The concentration of the above bleaching agent preferably ranges from 0.05 to 0.3 mol per liter of the solution having bleaching capability, and it is especially preferred that a design be made at 0.1 to 0.15 mol per liter for reducing the discharge to the environment. When the solution having bleaching capability is a bleaching solution, a bromide is preferably incorporated therein in an amount of 0.2 to 1 mol, more preferably 0.3 to 0.8 mol per liter.

Each component is incorporated in the replenisher of the solution having bleaching capability fundamentally in a concentration calculated by the following formula. This enables holding the concentration of the mother liquor constant.

$$CR = CT \times (V1+V2)/V1 + CP$$

CR: concentration of each component in the replenisher,
CT: concentration of the component in the mother liquor (processing tank solution),
V1: amount of replenisher having bleaching capability supplied per m$^2$ of photosensitive material (mL), and
V2: amount carried from previous bath by 1 m$^2$ of photosensitive material (mL).

In addition, a pH buffer is preferably incorporated in the bleaching solution, and it is especially preferred to incorporate a dicarboxylic acid of low odor such as succinic acid, maleic acid, malonic acid, glutaric acid or adipic acid. It is also preferred to use common bleaching accelerators listed in JP-A-53-95630, RD No. 17129 and U.S. Pat. No. 3,893,858.

The bleaching solution is preferably replenished with 50 to 1000 mL, more preferably 80 to 500 mL, and much more preferably 100 to 300 mL, of a bleaching replenisher per m$^2$ of the photosensitive material. Further, the bleaching solution is preferably aerated.

Compounds and processing conditions described on page 7, left lower column, line 10 to page 8, right lower column, line 19 of JP-A-4-125558 can be applied to a processing solution having fixing capability.

For enhancing the fixing velocity and preservability, it is especially preferred to incorporate compounds represented by the general formulae (I) and (II) of JP-A-6-301169 either individually or in combination in the processing solution having fixing capability. Further, the use of p-toluenesulfinic salts and sulfinic acids listed in JP-A-1-224762 is preferred from the viewpoint of enhancing the preservability.

Although the incorporation of an ammonium as a cation in the solution having bleaching capability or solution having fixing capability is preferred from the viewpoint of enhancing the desilverization ability, it is preferred that the amount of ammonium be reduced or brought to nil from the viewpoint of minimizing environmental pollution.

Conducting jet agitation described in JP-A-1-309059 is especially preferred in the bleach, bleach-fix and fixation steps.

The amount of replenisher supplied in the bleach-fix or fixation step is in the range of 100 to 1000 mL, preferably 150 to 700 mL, and especially preferably 200 to 600 mL, per $m^2$ of the photosensitive material.

Silver is preferably recovered by installing any of various silver recovering devices in an in-line or off-line mode in the bleach-fix or fixation step. In-line installation enables processing with the silver concentration of the solution lowered, so that the amount of replenisher can be reduced. It is also suitable to conduct an off-line silver recovery and recycle residual solution for use as a replenisher.

The bleach-fix and fixation steps can each be constructed by a plurality of processing tanks. Preferably, the tanks are provided with cascade piping and a multistage counterflow system is adopted. A 2-tank cascade structure is generally effective from the viewpoint of a balance with the size of the developing machine. The ratio of processing time in the former-stage tank to that in the latter-stage tank is preferably in the range of 0.5:1 to 1:0.5, more preferably 0.8:1 to 1:0.8.

From the viewpoint of enhancing the preservability, it is preferred that a chelating agent which is free without forming any metal complex be present in the bleach-fix and fixing solutions. Biodegradable chelating agents described in connection with the bleaching solution are preferably used as such a chelating agent.

Descriptions made on page 12, right lower column, line 6 to page 13, right lower column, line 16 of JP-A-4-125558 mentioned above can preferably be applied to water washing and stabilization steps. In particular, with respect to stabilizing solutions, the use of azolylmethylamines described in EP Nos. 504,609 and 519,190 and N-methylolazoles described in JP-A-4-362943 in place of formaldehyde and the dimerization of magenta coupler into a surfactant solution not containing an image stabilizer such as formaldehyde are preferred from the viewpoint of protecting working environment.

To reduce adhesion of dust to a magnetic recording layer formed on a photosensitive material, a stabilizer described in JP-A-6-289559 can be preferably used.

The replenishment rate of washing water and a stabilizer is preferably 80 to 1,000 mL, more preferably, 100 to 500 mL, and most preferably, 150 to 300 mL per $m^2$ of a photosensitive material in order to maintain the washing and stabilization functions and at the same time reduce the waste liquors for environmental protection. In processing performed with this replenishment rate, it is preferable to prevent the propagation of bacteria and mildew by using known mildewproofing agents such as thiabendazole, 1,2-benzoisothiazoline-3-one, and 5-chloro-2-methylisothiazoline-3-one, antibiotics such as gentamicin, and water deionized by an ion exchange resin or the like. It is more effective to use deionized water together with a mildewproofing agent or an antibiotic.

The replenishment rate of a solution in a washing water tank or stabilizer tank is preferably reduced by performing reverse permeable membrane processing described in JP-A's-3-46652, 3-53246, 3-55542, 3-121448, and 3-126030. A reverse permeable membrane used in this processing is preferably a low-pressure reverse permeable membrane.

In the processing of the present invention, it is particularly preferable to perform processing solution evaporation correction disclosed in Journal of Technical Disclosure No. 94-4992. In particular, a method of performing correction on the basis of (formula-1) on page 2 by using temperature and humidity information of an environment in which a processor is installed is preferable. Water for use in this evaporation correction is preferably taken from the washing water replenishment tank. If this is the case, deionized water is preferably used as the washing replenishing water.

Processing agents described in aforementioned Journal of Technical Disclosure No. 94-4992, page 3, right column, line 15 to page 4, left column, line 32 are preferably used in the present invention. As a processor for these processing agents, a film processor described on page 3, right column, lines 22 to 28 is preferable.

Practical examples of processing agents, automatic processors, and evaporation correction methods suited to practicing the present invention are described in the same Journal of Technical Disclosure No. 94-4992, page 5, right column, line 11 to page 7, right column, last line.

Processing agents used in the present invention can be supplied in any form: a liquid agent having the concentration of a solution to be used, concentrated liquid agent, granules, powder, tablets, paste, and emulsion. Examples of such processing agents are a liquid agent contained in a low-oxygen permeable vessel disclosed in JP-A-63-17453, vacuum-packed powders and granules disclosed in JP-A's-4-19655 and 4-230748, granules containing a water-soluble polymer disclosed in JP-A-4-221951, tablets disclosed in JP-A's-51-61837 and 6-102628, and a paste disclosed in PCT KOHYO Publication No. 57-500485. Although any of these processing agents can be preferably used, the use of a liquid adjusted to have the concentration of a solution to be used is preferable for the sake of convenience in use.

As a vessel for containing these processing agents, polyethylene, polypropylene, polyvinylchloride, polyethyleneterephthalate, and nylon are used singly or as a composite material. These materials are selected in accordance with the level of necessary oxygen permeability. For a readily oxidizable solution such as a color developer, a low-oxygen permeable material is preferable. More specifically, polyethyleneterephthalate or a composite material of polyethylene and nylon is preferable. A vessel made of any of these materials preferably has a thickness of 500 to 1,500 mm and an oxygen permeability of 20 $mL/m^2 \cdot 24$ hrs·atm or less.

Color reversal film processing solutions used in the present invention will be described below. Processing for a color reversal film is described in detail in Aztech Ltd., Known Technology No. 6 (Apr. 1, 1991), page 1, line 5 to page 10, line 5 and page 15, line 8 to page 24, line 2, and any of the contents can be preferably applied. In this color reversal film processing, an image stabilizing agent is contained in a control bath or a final bath. Preferable examples of this image stabilizing agent are formalin, sodium formaldehyde-bisulfite, and N-methylolazole. Sodium formaldehyde-bisulfite or N-methylolazole is preferable in terms of work environment, and N-methyloltriazole is particularly preferable as N-methylolazole. The contents pertaining to a color developer, bleaching solution, fixing solution, and washing water described in the color negative film processing can be preferably applied to the color reversal film processing.

Preferable examples of color reversal film processing agents containing the above contents are an E-6 processing agent manufactured by Eastman Kodak Co. and a CR-56 processing agent manufactured by Fuji Photo Film Co., Ltd.

EXAMPLES

Example-1

The present invention will be described specifically by examples of the present invention, but the present invention is not limited to these examples.

Preparation of Sample 101

(1) Preparation of Triacetylcellulose Film

Triacetylcellulose film was formed according to the band method by subjecting to customary solution casting a solution wherein triacetylcellulose (13% by weight) was dissolved in a 92:8 (weight ratio) mixture of dichloromethane and methanol, with the plasticizer changed to a 2:1 by weight mixture of triphenyl phosphate and biphenyldiphenyl phosphate amounting to 14% based on triacetylcellulose. The support after drying had a thickness of 205 μm.

(2) Components of Undercoat Layer

The two surfaces of the triacetylcellulose film were subjected to undercoating treatment. Numbers represent weight contained per liter of an undercoat solution. The two surfaces of the triacetylcellulose film were subjected to corona discharge treatment before undercoating treatment.

| | |
|---|---|
| Gelatin | 10.0 g |
| Salicylic acid | 0.3 g |
| Glycerin | 3.0 g |
| Acetone | 700 mL |
| Methanol | 150 mL |
| Dichloromethane | 80 mL |
| Formaldehyde | 0.1 mg |
| Water to make | 1.0 L |

(3) Coating of Back Layers

One surface of the undercoated support was coated with the following back layers.

| | |
|---|---|
| 1st layer | |
| Binder: acid-processed gelatin (isoelectric point: 9.0) | 1.00 g |
| Polymeric latex: P-2 (average grain size: 0.1 μm) | 0.13 g |
| Polymeric latex: P-3 (average grain size 0.2 μm) | 0.23 g |
| Ultraviolet absorbent U-1 | 0.030 g |
| Ultraviolet absorbent U-3 | 0.010 g |
| Ultraviolet absorbent U-4 | 0.020 g |
| High-boiling organic solvent Oil-2 | 0.030 g |
| Surfactant W-3 | 0.010 g |
| Surfactant W-6 | 3.0 mg |
| 2nd layer | |
| Binder: acid-processed gelatin (isoelectric point: 9.0) | 3.10 g |
| Polymeric latex: P-3 (average grain size: 0.2 μm) | 0.11 g |
| Ultraviolet absorbent U-1 | 0.030 g |
| Ultraviolet absorbent U-3 | 0.010 g |
| Ultraviolet absorbent U-4 | 0.020 g |
| High-boiling organic solvent Oil-2 | 0.030 g |
| Surfactant W-3 | 0.010 g |
| Surfactant W-6 | 3.0 mg |
| Dye D-2 | 0.10 g |
| Dye D-10 | 0.12 g |
| Potassium sulfate | 0.25 g |
| Calcium chloride | 0.5 mg |
| Sodium hydroxide | 0.03 g |
| 3rd layer | |
| Binder: acid-processed gelatin (isoelectric point: 9.0) | 3.30 g |
| Surfactant W-3 | 0.020 g |
| Potassium sulfate | 0.30 g |
| Sodium hydroxide | 0.03 g |
| 4th layer | |
| Binder: lime-processed gelatin (isoelectric point: 5.4) | 1.15 g |
| 1:9 copolymer of methacrylic acid and methylmethacrylate (average grain size: 2.0 μm) | 0.040 g |
| 6:4 copolymer of methacrylic acid and methylmethacrylate (average grain size: 2.0 μm) | 0.030 g |
| Surfactant W-3 | 0.060 g |
| Surfactant W-2 | 7.0 mg |
| Hardener H-1 | 0.23 g |

(4) Application of Lightsensitive Emulsion Layers by Coating:

The following lightsensitive emulsion layers were applied to the side of support opposite to that coated with the back layer, thereby obtaining sample 101. The figures given below indicate the addition amount per m². The effects of added compounds are not limited to the described usage.

| | | |
|---|---|---|
| 1st layer (Antihalation layer) | | |
| Black colloidal silver | | 0.30 g |
| Gelatin | | 2.50 g |
| Ultraviolet absorber U-1 | | 0.10 g |
| Ultraviolet absorber U-3 | | 0.10 g |
| Ultraviolet absorber U-4 | | 0.10 g |
| Ultraviolet absorber U-5 | | 0.15 g |
| High-boiling organic solvent Oil-1 | | 0.10 g |
| High-boiling organic solvent Oil-2 | | 0.10 g |
| Dye D-4 | | 1.0 mg |
| Dye D-8 | | 2.5 mg |
| Fine crystalline solid dispersion of dye E-1 | | 0.05 g |
| 2nd layer (Interlayer) | | |
| Gelatin | | 0.50 g |
| Compound Cpd-A | | 0.2 mg |
| Compound Cpd-K | | 4.0 mg |
| Compound Cpd-M | | 0.030 g |
| Ultraviolet absorber U-6 | | 6.0 mg |
| High-boiling organic solvent Oil-3 | | 0.010 g |
| High-boiling organic solvent Oil-4 | | 0.010 g |
| High-boiling organic solvent Oil-7 | | 2.0 mg |
| Dye D-7 | | 4.0 mg |
| 3rd layer (Interlayer) | | |
| Yellow colloidal silver | | 0.020 g |
| Gelatin | | 0.60 g |
| Compound Cpd-D | | 0.020 g |
| High-boiling organic solvent Oil-3 | | 0.010 g |
| High-boiling organic solvent Oil-8 | | 0.010 g |
| 4th layer (Low-speed red-sensitive emulsion layer) | | |
| Emulsion A | silver | 0.30 g |
| Emulsion B | silver | 0.15 g |
| Emulsion C | silver | 0.10 g |
| Gelatin | | 0.80 g |
| Coupler C-1 | | 0.10 g |
| Coupler C-2 | | 0.050 g |
| Ultraviolet absorber U-3 | | 0.010 g |
| Compound Cpd-I | | 0.020 g |
| Compound Cpd-D | | 3.0 mg |
| Compound Cpd-J | | 2.0 mg |
| High-boiling organic solvent Oil-2 | | 0.070 g |
| 5th layer (Medium-speed red-sensitive emulsion layer) | | |
| Emulsion C | silver | 0.25 g |
| Emulsion D | silver | 0.25 g |
| Gelatin | | 0.60 g |
| Coupler C-1 | | 0.20 g |
| Coupler C-2 | | 0.080 g |

-continued

| | | |
|---|---|---|
| Compound Cpd-D | | 3.0 mg |
| Ultraviolet absorber U-3 | | 0.010 g |
| High-boiling organic solvent Oil-2 | | 0.10 g |
| Additive P-1 | | 2.0 mg |
| 6th layer (High-speed red-sensitive emulsion layer) | | |
| Emulsion E | silver | 0.20 g |
| Emulsion F | silver | 0.25 g |
| Gelatin | | 1.70 g |
| Coupler C-1 | | 0.10 g |
| Coupler C-2 | | 0.10 g |
| Coupler C-3 | | 0.60 g |
| High-boiling organic solvent Oil-2 | | 0.050 g |
| Compound Cpd-F | | 0.030 g |
| Additive P-1 | | 5.0 mg |
| 7th layer (Interlayer) | | |
| Gelatin | | 0.80 g |
| Additive P-2 | | 0.10 g |
| Dye D-5 | | 0.020 g |
| Dye D-9 | | 6.0 mg |
| Compound Cpd-I | | 0.010 g |
| Compound Cpd-M | | 0.10 g |
| Compound Cpd-O | | 3.0 mg |
| Compound Cpd-P | | 5.0 mg |
| High-boiling organic solvent Oil-6 | | 0.050 g |
| 8th layer (Interlayer) | | |
| Yellow colloidal silver | silver | 0.020 g |
| Gelatin | | 1.20 g |
| Additive P-2 | | 0.05 g |
| Ultraviolet absorber U-1 | | 0.010 g |
| Ultraviolet absorber U-3 | | 0.010 g |
| Compound Cpd-A | | 0.020 g |
| Compound Cpd-D | | 0.030 g |
| Compound Cpd-M | | 0.050 g |
| Compound Cpd-L | | 3.0 mg |
| High-boiling organic solvent Oil-3 | | 0.010 g |
| High-boiling organic solvent Oil-6 | | 0.050 g |
| 9th layer (Low-speed green-sensitive emulsion layer) | | |
| Emulsion G | silver | 0.20 g |
| Emulsion H | silver | 0.30 g |
| Emulsion I | silver | 0.30 g |
| Gelatin | | 1.50 g |
| Coupler C-4 | | 0.25 g |
| Coupler C-5 | | 0.050 g |
| Coupler C-6 | | 0.020 g |
| Coupler C-7 | | 0.010 g |
| Compound Cpd-B | | 0.030 g |
| Compound Cpd-D | | 5.0 mg |
| Compound Cpd-G | | 2.5 mg |
| Compound Cpd-F | | 0.010 g |
| Compound Cpd-K | | 2.0 mg |
| Ultraviolet absorber U-6 | | 5.0 mg |
| High-boiling organic solvent Oil-2 | | 0.15 g |
| 10th layer (Medium-speed green-sensitive emulsion layer) | | |
| Emulsion I | silver | 0.25 g |
| Emulsion J | silver | 0.25 g |
| Gelatin | | 0.90 g |
| Coupler C-4 | | 0.050 g |
| Coupler C-5 | | 0.050 g |
| Coupler C-6 | | 0.30 g |
| Coupler C-7 | | 0.010 g |
| Compound Cpd-B | | 0.030 g |
| Compound Cpd-F | | 0.010 g |
| Compound Cpd-G | | 2.0 mg |
| High-boiling organic solvent Oil-2 | | 0.030 g |
| 11th layer (High-speed green-sensitive emulsion layer) | | |
| Emulsion K | silver | 0.45 g |
| Gelatin | | 0.80 g |
| Coupler C-6 | | 0.50 g |
| Coupler C-7 | | 5.0 mg |
| Compound Cpd-A | | 5.0 mg |
| Compound Cpd-B | | 0.030 g |

-continued

| | | |
|---|---|---|
| Compound Cpd-F | | 0.010 g |
| High-boiling organic solvent Oil-2 | | 0.030 g |
| 12th layer (Yellow filter layer) | | |
| Yellow colloidal silver | silver | 0.010 g |
| Gelatin | | 1.0 g |
| Compound Cpd-C | | 0.010 g |
| Compound Cpd-M | | 0.10 g |
| High-boiling organic solvent Oil-6 | | 0.10 g |
| Fine crystalline solid dispersion of dye E-2 | | 0.25 g |
| 13th layer (Interlayer) | | |
| Gelatin | | 0.40 g |
| Compound Cpd-Q | | 0.20 g |
| High-boiling organic solvent Oil-5 | | 0.020 g |
| Dye D-6 | | 3.0 mg |
| 14th layer (Low-speed blue-sensitive emulsion layer) | | |
| Emulsion L | silver | 0.10 g |
| Emulsion M | silver | 0.20 g |
| Emulsion N | silver | 0.10 g |
| Gelatin | | 1.00 g |
| Coupler C-8 | | 0.020 g |
| Coupler C-9 | | 0.35 g |
| Coupler C-10 | | 5.0 mg |
| Compound Cpd-B | | 0.10 g |
| Compound Cpd-I | | 8.0 mg |
| Compound Cpd-K | | 1.0 mg |
| Ultraviolet absorber U-6 | | 0.010 g |
| High-boiling organic solvent Oil-2 | | 0.010 g |
| 15th layer (Medium-speed blue-sensitive emulsion layer) | | |
| Emulsion N | silver | 0.15 g |
| Emulsion O | silver | 0.20 g |
| Gelatin | | 0.80 g |
| Coupler C-8 | | 0.020 g |
| Coupler C-9 | | 0.40 g |
| Coupler C-10 | | 0.010 g |
| Compound Cpd-B | | 0.10 g |
| Compound Cpd-N | | 2.0 mg |
| High-boiling organic solvent Oil-2 | | 0.010 g |
| 16th layer (High-speed blue-sensitive emulsion layer) | | |
| Emulsion P | silver | 0.20 g |
| Emulsion Q | silver | 0.25 g |
| Gelatin | | 2.00 g |
| Coupler C-3 | | 5.0 mg |
| Coupler C-8 | | 0.10 g |
| Coupler C-9 | | 1.00 g |
| Coupler C-10 | | 0.020 g |
| High-boiling organic solvent Oil-2 | | 0.10 g |
| High-boiling organic solvent Oil-3 | | 0.020 g |
| Ultraviolet absorber U-6 | | 0.10 g |
| Compound Cpd-B | | 0.20 g |
| Compound Cpd-N | | 5.0 mg |
| 17th layer (1st protective layer) | | |
| Gelatin | | 1.00 g |
| Ultraviolet absorber U-1 | | 0.10 g |
| Ultraviolet absorber U-2 | | 0.050 g |
| Ultraviolet absorber U-5 | | 0.30 g |
| Compound Cpd-O | | 5.0 mg |
| Compound Cpd-A | | 0.030 g |
| Compound Cpd-H | | 0.20 g |
| Dye D-1 | | 8.0 mg |
| Dye D-2 | | 0.010 g |
| Dye D-3 | | 0.010 g |
| High-boiling organic solvent Oil-3 | | 0.10 g |
| 18th layer (2nd protective layer) | | |
| Colloidal silver | silver | 2.0 mg |
| Fine-grain silver iodobromide emulsion (silver iodide content 1 mol %, equivalent sphere average grain diameter 0.06 μm) | silver | 0.10 g |
| Gelatin | | 0.80 g |
| Ultraviolet absorber U-1 | | 0.030 g |

-continued

| | |
|---|---|
| Ultraviolet absorber U-6 | 0.030 g |
| High-boiling organic solvent Oil-3 | 0.010 g |
| 19th layer (3rd protective layer) | |
| Gelatin | 1.00 g |
| Polymethyl methacrylate (average particle size 1.5 μm) | 0.10 g |
| Methyl methacrylate/methacrylic acid 6:4 copolymer (average particle size 1.5 μm) | 0.15 g |
| Silicone oil SO-1 | 0.20 g |
| Surfactant W-1 | 3.0 mg |
| Surfactant W-2 | 8.0 mg |
| Surfactant W-3 | 0.040 g |
| Surfactant W-7 | 0.015 g |

In addition to the above compositions, additives F-1 to F-9 were added to all the above emulsion layers. Furthermore, in addition to the above compositions, gelatin hardener H-1 and surfactants for coating and emulsification W-3, W-4, W-5 and W-6 were added to each of the above layers.

Still further, phenol, 1,2-benzisothiazolin-3-one, 2-phenoxyethanol, phenethyl alcohol and p-(n)-butyl benzoate were added as antiseptics and mildewproofing agents.

TABLE 1

Silver iodobromide emulsions used in sample 101

| Emulsion | Characteristics | Av. ESD (μm) | COV (%) | Av. AgI content (mol %) | Structure in halide composition of silver halide grains | AgI content at grain surface (mol %) | Other characteristics | | | | |
|---|---|---|---|---|---|---|---|---|---|---|---|
| | | | | | | | (1) | (2) | (3) | (4) | (5) |
| A | Monodispersed tetradecahedral grains | 0.24 | 10 | 3.5 | Double structure | 1.5 | ○ | | | | |
| B | Monodispersed (111) tabular grains Av. aspect ratio 3.0 | 0.25 | 10 | 3.5 | Triple structure | 1.5 | ○ | | | ○ | ○ |
| C | Monodispersed (111) tabular grains Av. aspect ratio 8.0 | 0.30 | 19 | 3.5 | Triple structure | 0.1 | ○ | | | | ○ |
| D | Monodispersed (111) tabular grains Av. aspect ratio 8.0 | 0.40 | 21 | 4.0 | Triple structure | 2.0 | ○ | ○ | | ○ | ○ |
| E | Monodispersed (111) tabular grains Av. aspect ratio 10.0 | 0.50 | 10 | 1.0 | Quadruple structure | 1.5 | ○ | | | | |
| F | Monodispersed (111) tabular grains Av. aspect ratio 10.5 | 0.70 | 12 | 1.6 | Triple structure | 0.6 | ○ | ○ | | | ○ |
| G | Monodispersed cubic grains | 0.15 | 9 | 3.5 | Triple structure | 2.0 | | | ○ | | |
| H | Monodispersed cubic grains | 0.24 | 12 | 4.9 | structure | 0.1 | | ○ | | ○ | |
| I | Monodispersed (111) tabular grains Av. aspect ratio 4.0 | 0.35 | 12 | 3.5 | Quintuple structure | 4.5 | | ○ | | ○ | ○ |
| J | Monodispersed (111) tabular grains Av. aspect ratio 10.0 | 0.45 | 21 | 3.0 | Quadruple structure | 0.2 | ○ | ○ | | | ○ |
| K | Monodispersed (111) tabular grains Av. aspect ratio 10.5 | 0.65 | 13 | 2.7 | Triple structure | 1.3 | ○ | ○ | | | ○ |
| L | Monodispersed tetradecahedral grains | 0.31 | 9 | 7.5 | Triple structure | 7.0 | | | ○ | | ○ |
| M | Monodispersed tetradecahedral grains | 0.31 | 9 | 7.5 | Triple structure | 5.0 | ○ | | | ○ | ○ |
| N | Monodispersed (111) tabular grains Av. aspect ratio 10.0 | 0.33 | 13 | 2.1 | Quadruple structure | 4.0 | ○ | ○ | ○ | | |
| O | Monodispersed (111) tabular grains Av. aspect ratio 12.0 | 0.50 | 9 | 2.5 | Quadruple structure | 1.0 | | ○ | | | ○ |
| P | Monodispersed (111) tabular grains Av. aspect ratio 12.0 | 0.75 | 21 | 2.8 | Triple structure | 0.5 | ○ | ○ | | | ○ |

TABLE 1-continued

Silver iodobromide emulsions used in sample 101

| Emulsion | Characteristics | Av. ESD (μm) | COV (%) | Av. AgI content (mol %) | Structure in halide composition of silver halide grains | AgI content at grain surface (mol %) | Other characteristics (1) | (2) | (3) | (4) | (5) |
|---|---|---|---|---|---|---|---|---|---|---|---|
| Q | Monodispersed (111) tabular grains Av. aspect ratio 12.0 | 0.85 | 8 | 1.0 | Quadruple structure | 0.5 | ○ | ○ | | | ○ |

Av. ESD = Equivalent sphere average grain size;
COV = Coefficient of variation
(Other characteristics)
The mark "○" means each of the conditions set forth below is satisfied.
(1) A reduction sensitizer was added during grain formation;
(2) A selenium sensitizer was used as an after-ripening agen;
(3) A rhodium salt was added during grain formation;
(4) A shell was provided subsequent to after-ripening by using silver nitrate in an amount of 10%, in terms of silver molar ratio, of the emulsion grains at that time, together with the equimolar amount of potassium bromide; and
(5) The presence of dislocation lines in an average number of ten or more per grain was observed by a transmission electron microscope.
Note that all the lightsensitive emulsion were after-ripped by the use of sodium thiosulfate, sodium thiocyanate, and sodium aurichloride.
Note, also, a iridium salt was added during grain formation.
Note, also, that chemically-modified gelatin whose amino groups were partially converted to phthalic acid amide, was added to emulsions B, C, E, H, J, N, and Q.

TABLE 2

| Emulsion | Spectral sensitizer added | Addition amount per mol of silver halide (g) | Timing of the addition of the spectral sensitizer |
|---|---|---|---|
| A | S-1 | 0.01 | Subsequent to after-ripening |
|  | S-2 | 0.20 | Before after-ripening |
|  | S-3 | 0.02 | Before after-ripening |
|  | S-8 | 0.25 | Before after-ripening |
|  | S-13 | 0.015 | Before after-ripening |
|  | S-14 | 0.01 | Before after-ripening |
| B | S-2 | 0.20 | Before after-ripening |
|  | S-3 | 0.02 | Before after-ripening |
|  | S-8 | 0.20 | Before after-ripening |
|  | S-13 | 0.015 | Before after-ripening |
|  | S-14 | 0.01 | Before after-ripening |
| C | S-2 | 0.25 | Before after-ripening |
|  | S-3 | 0.04 | Before after-ripening |
|  | S-8 | 0.25 | Before after-ripening |
|  | S-13 | 0.02 | Subsequent to after-ripening |
|  | S-14 | 0.04 | Subsequent to after-ripening |
| D | S-2 | 0.25 | Before after-ripening |
|  | S-3 | 0.03 | Before after-ripening |
|  | S-8 | 0.25 | Before after-ripening |
|  | S-13 | 0.01 | Before after-ripening |
| E | S-1 | 0.01 | Subsequent to after-ripening |
|  | S-2 | 0.20 | Before after-ripening |
|  | S-3 | 0.05 | Before after-ripening |
|  | S-8 | 0.25 | Before after-ripening |
|  | S-13 | 0.01 | Before after-ripening |
|  | S-14 | 0.02 | Before after-ripening |
| F | S-2 | 0.20 | Before after-ripening |
|  | S-3 | 0.04 | Before after-ripening |
|  | S-8 | 0.20 | Before after-ripening |
|  | S-14 | 0.02 | Before after-ripening |
| G | S-4 | 0.3 | Subsequent to after-ripening |
|  | S-5 | 0.05 | Subsequent to after-ripening |
|  | S-12 | 0.1 | Subsequent to after-ripening |
| H | S-4 | 0.2 | Before after-ripening |
|  | S-5 | 0.05 | Subsequent to after-ripening |
|  | S-9 | 0.15 | Before after-ripening |
|  | S-14 | 0.02 | Subsequent to after-ripening |
| I | S-4 | 0.3 | Before after-ripening |
|  | S-9 | 0.2 | Before after-ripening |
|  | S-12 | 0.1 | Before after-ripening |
| J | S-4 | 0.35 | Before after-ripening |
|  | S-5 | 0.05 | Subsequent to after-ripening |
|  | S-12 | 0.1 | Before after-ripening |
| K | S-4 | 0.3 | Before after-ripening |
|  | S-9 | 0.05 | Before after-ripening |
|  | S-12 | 0.1 | Before after-ripening |
|  | S-14 | 0.02 | Before after-ripening |
| L,M | S-6 | 0.1 | Subsequent to after-ripening |
|  | S-10 | 0.2 | Subsequent to after-ripening |
|  | S-11 | 0.05 | Subsequent to after-ripening |
| N | S-6 | 0.05 | Subsequent to after-ripening |
|  | S-7 | 0.05 | Subsequent to after-ripening |
|  | S-10 | 0.25 | Subsequent to after-ripening |
|  | S-11 | 0.05 | Subsequent to after-ripening |
| O | S-10 | 0.4 | Subsequent to after-ripening |
|  | S-11 | 0.15 | Subsequent to after-ripening |
| P | S-6 | 0.05 | Subsequent to after-ripening |
|  | S-7 | 0.05 | Subsequent to after-ripening |
|  | S-10 | 0.3 | Before after-ripening |
|  | S-11 | 0.1 | Before after-ripening |
| Q | S-6 | 0.05 | Before after-ripening |
|  | S-7 | 0.05 | Before after-ripening |
|  | S-10 | 0.2 | Before after-ripening |
|  | S-11 | 0.25 | Before after-ripening |

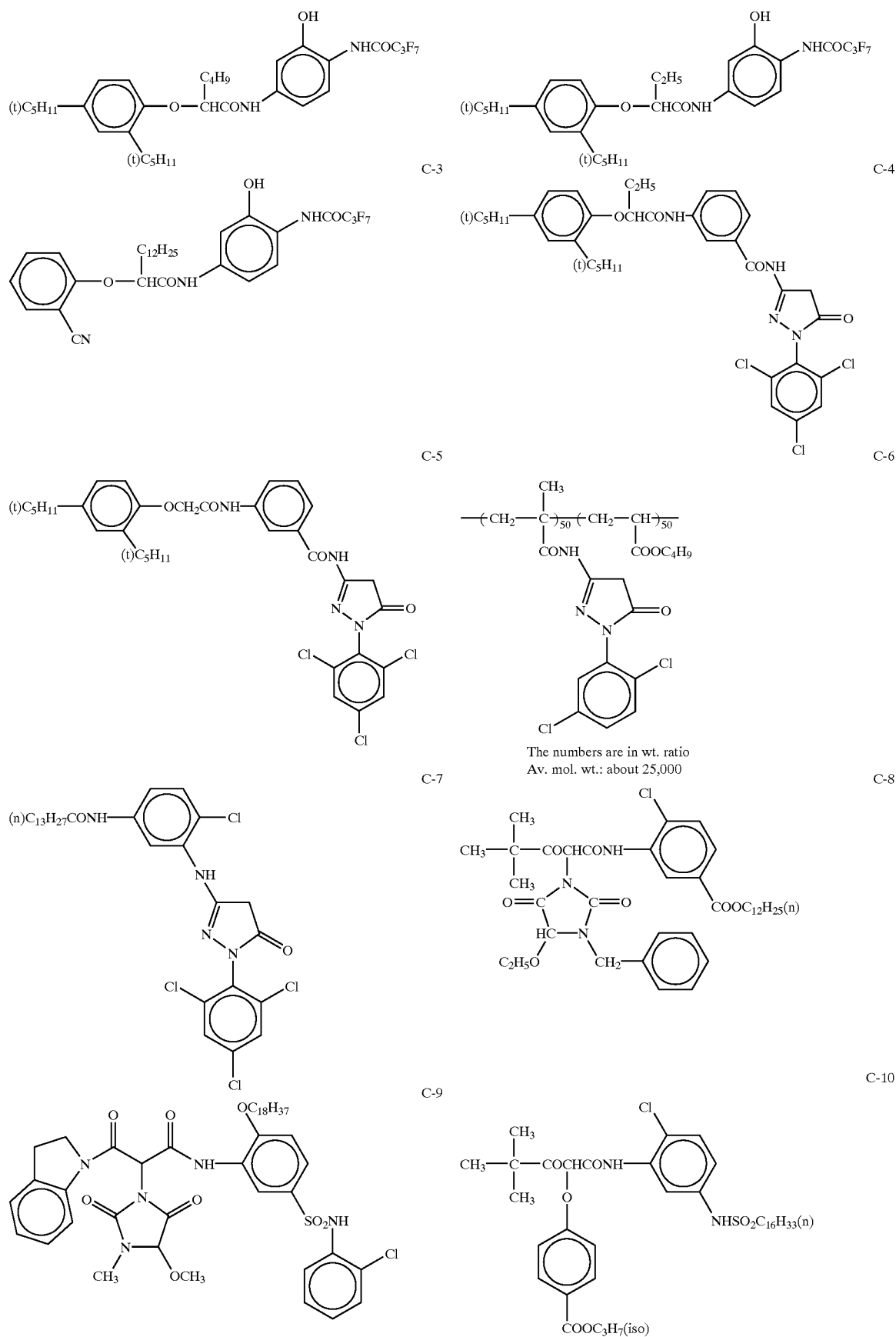

Oil-1 Tri-n-hexyl phosphate
Oil-2 Tricresyl phosphate
Oil-3 Tricyclohexyl phosphate
Oil-4
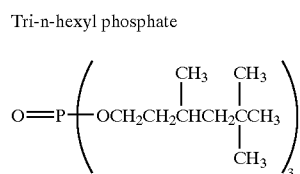
Oil-5
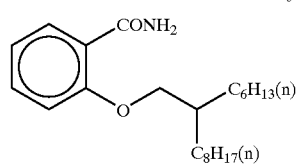
Oil-6
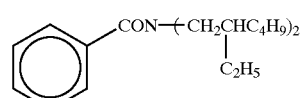
Oil-7
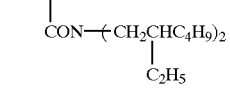
Oil-8
Cpd-A
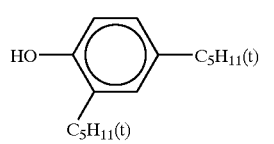
Cpd-B
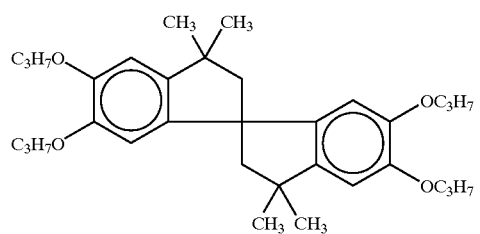
Cpd-C
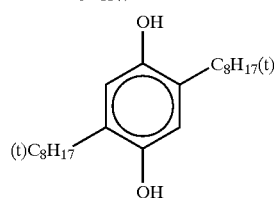
Cpd-D
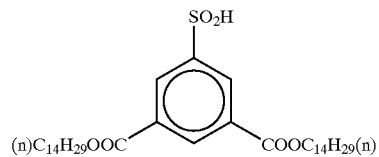
Cpd-F
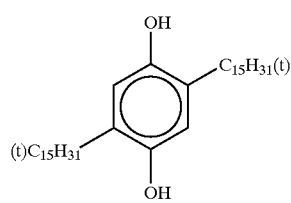
Cpd-G
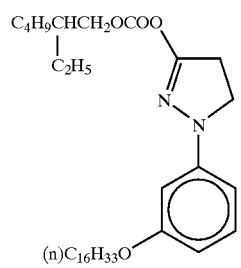
Cpd-H
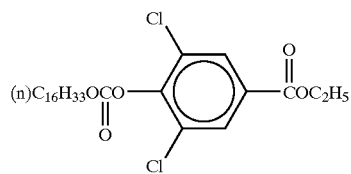
Cpd-I
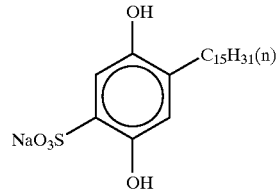
Cpd-J
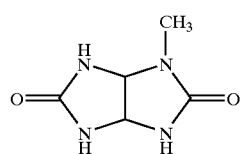
Cpd-K
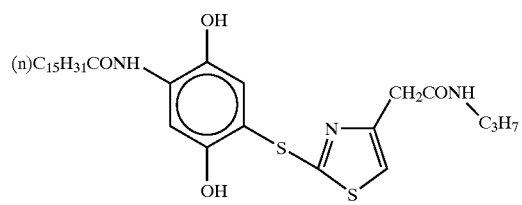
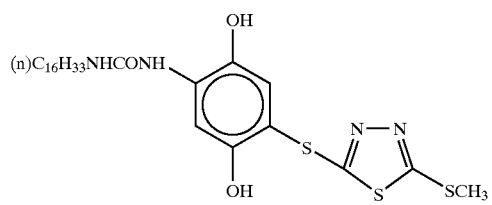

-continued
Cpd-L 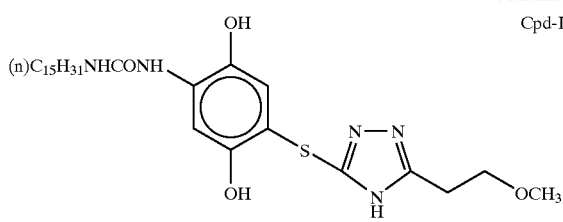 Cpd-M 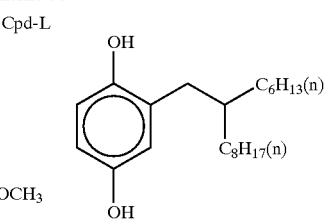
Cpd-N 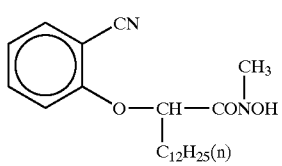 Cpd-O 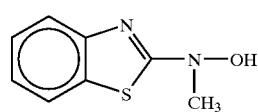
Cpd-P 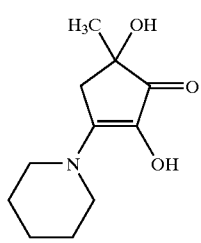 Cpd-Q CH₂—NH\
                                           >C=O\
                                  CH₂—NH
U-1 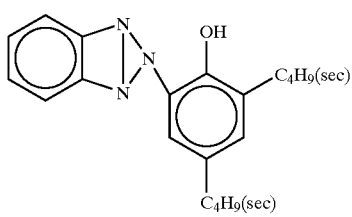 U-2 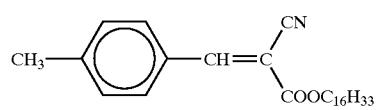
U-3 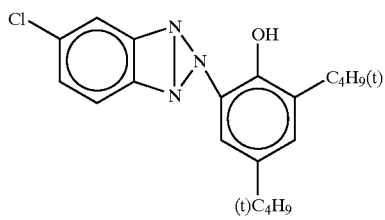 U-4 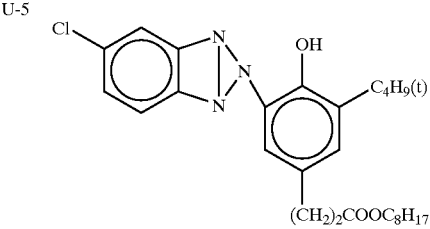
U-5 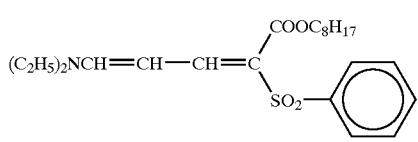 U-6
S-1 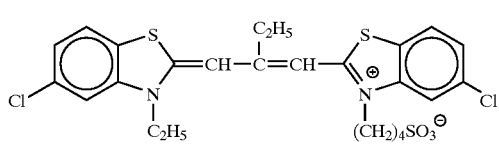 S-2 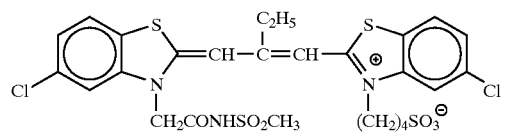

-continued
S-3
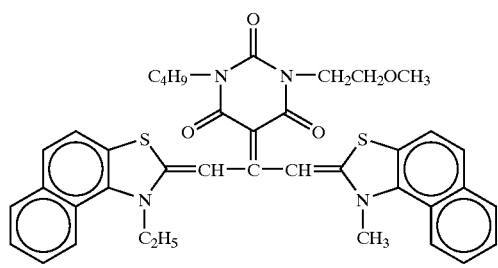
S-4
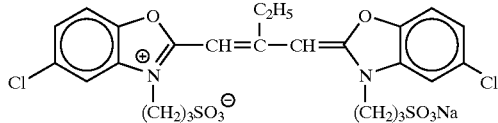
S-5
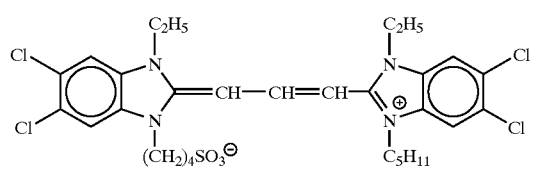
S-6
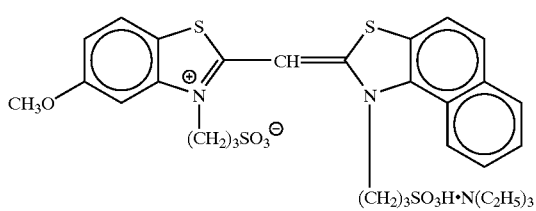
S-7
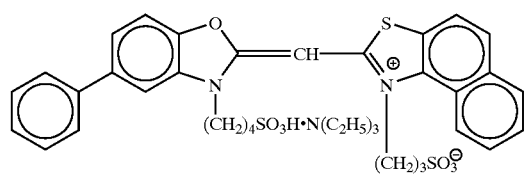
S-8
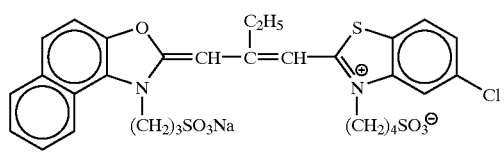
S-9
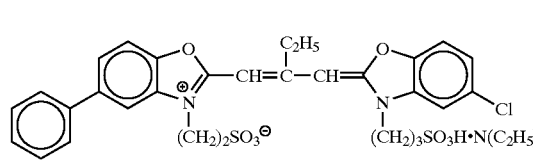
S-10
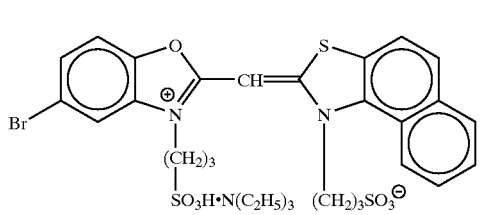
S-11
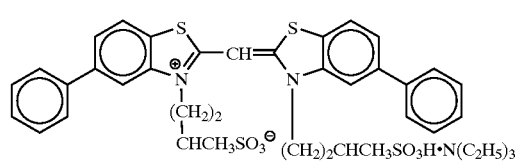
S-12
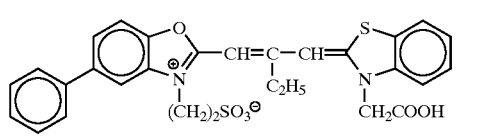
S-13
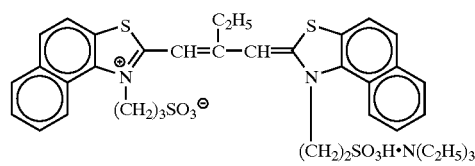
S-14
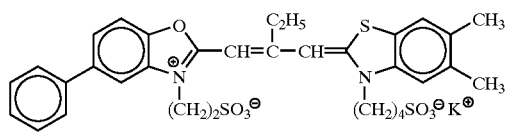
D-1
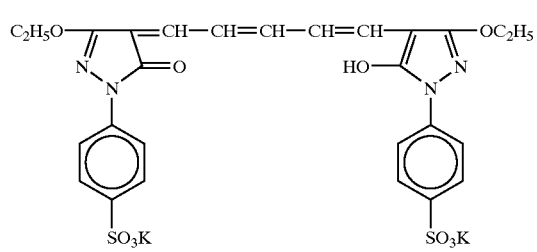
D-2
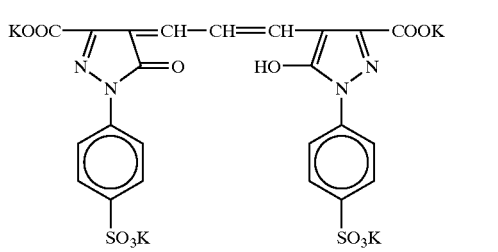

-continued
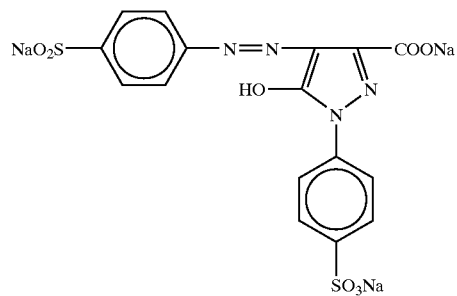
D-3
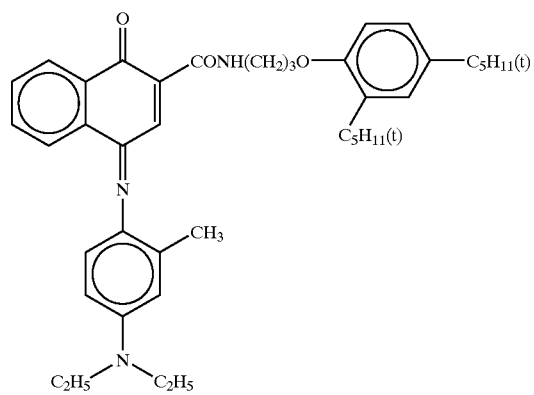
D-4
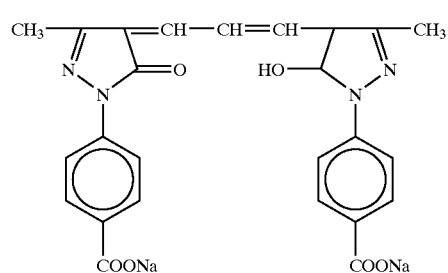
D-5
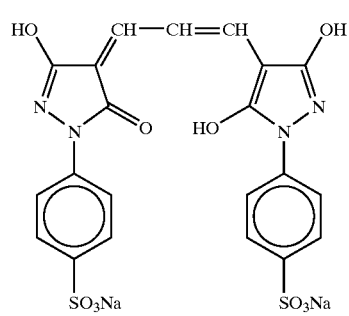
D-6
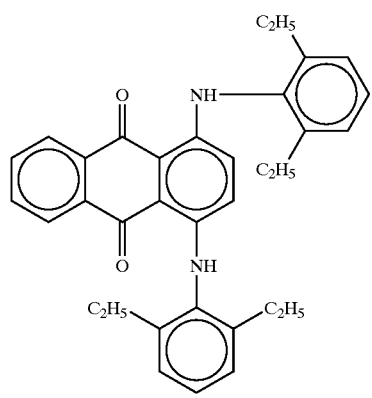
D-7
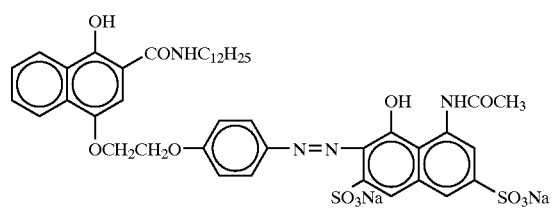
D-8
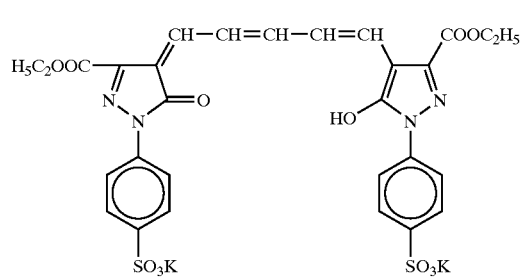
D-9 D-10
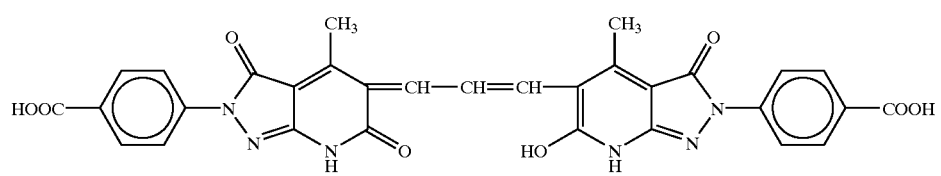
E-1

-continued

-continued
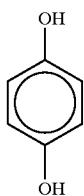
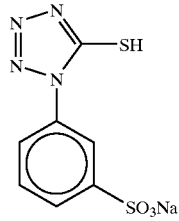
F-5
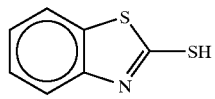
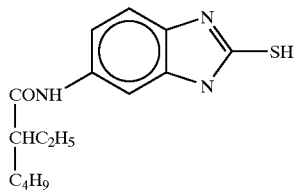
F-7
F-6
F-8
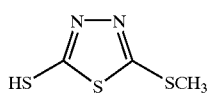
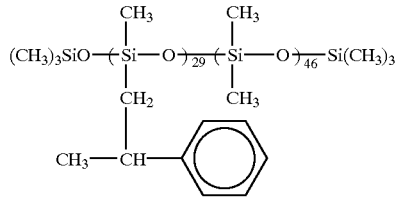
F-9      SO-1
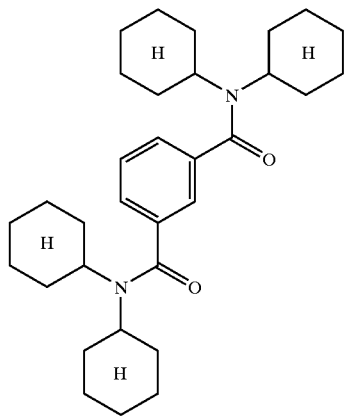
Oil-A
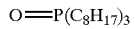
O=P(C$_8$H$_{17}$)$_3$
Oil-B
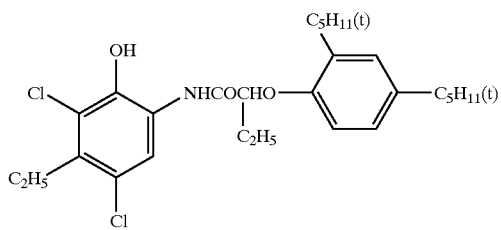
CC-1
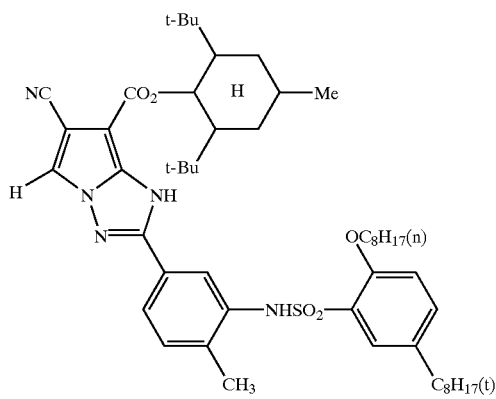
Comparative coupler (a)

-continued

Comparative coupler (b)

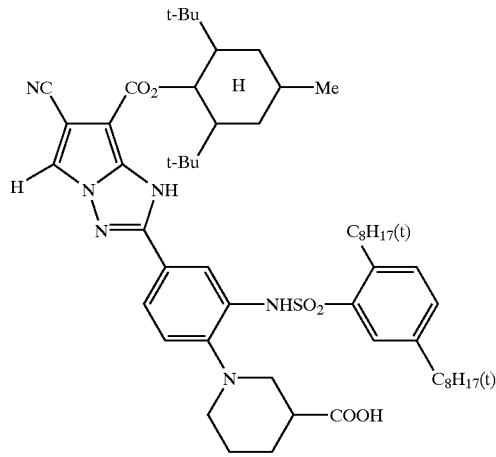

Comparative coupler (c)

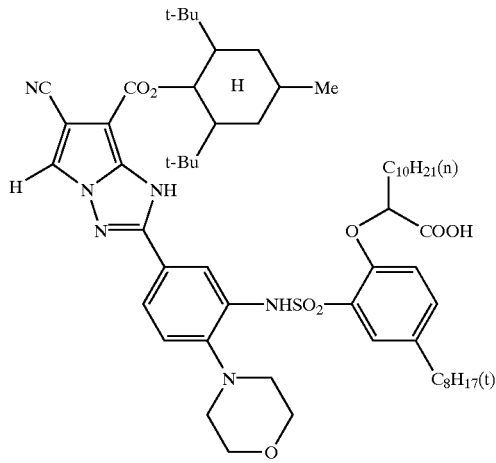

Preparation of Fine Crystalline Solid Dispersion of Organic Dye:

(Preparation of Fine Crystalline Solid Dispersion of Dye E-1)

Water and 100 g of Pluronic F88 (trade name for ethylene oxide/propylene oxide block copolymer) produced by BASF were added to a wet cake of dye E-1 (containing 270 g of dye E-1 in net weight), and agitated, thereby obtaining 4000 g of a slurry. Subsequently, 1700 mL of zirconia beads having an average grain diameter of 0.5 mm were charged into Ultraviscomill (UVM-2) manufactured by Aimex Co., Ltd. and the slurry was milled at a peripheral speed of 10 m/sec and a delivery of 0.5 L/min for 2 hr. The beads were removed by filtration, and the slurry was diluted with water into a dye concentration of 3%. The dilution was heated at 90° C. for 10 hr for stabilization. The obtained dye fine particles had an average particle diameter of 0.30 μm and a particle diameter distribution breadth (standard deviation of particle diameters×100/average particle diameter) of 20%.

(Preparation of Microcrystalline Solid Dispersion of Dye E-2)

Water and 270 g of W-4 were added to 1400 g of a wet cake of dye E-2 containing 30% by weight of water, and agitated, thereby obtaining a slurry of 40% by weight E-2 concentration. Subsequently, 1700 mL of zirconia beads having an average grain diameter of 0.5 mm were charged into a pulverizer, namely, Ultraviscomill (UVM-2) manufactured by Aimex Co., Ltd., and the slurry was milled at a peripheral speed of 10 m/sec and a delivery of 0.5 L/min for 8 hr. Thus, a solid fine particle dispersion of dye E-2 was obtained. This dispersion was diluted with ion-exchanged water to a concentration of 20% by weight. Thus, a microcrystalline solid dispersion was obtained. The average particle diameter thereof was 0.15 μm.

Next, couplers C-1, C-2 and C-3 in the 4th, 5th and 6th layers were changed as set forth in Table 3, thereby to make Samples 102 to 119. When the couplers C-1, C-2 and C-3 were replaced with the couplers of the present invention or comparative couplers set forth below, the couplers C-1 and C-2 were substituted so that the amount of each of the couplers of the invention and the comparative couplers becomes 0.5 times in molar ratio of each of the couplers C-1 and C-2, and the coupler C-3 was substituted so that the amount of each of the couplers of the invention and the comparative couplers becomes 0.55 times in molar ratio of the coupler C-3. Also, the amount of the high-boiling organic solvent in each layer was changed as set forth in Table 3 (the amount is shown in weight ratio to the coupler). The amount of the silver halide in each layer was changed as set forth below. Other additives were not changed.

| 4th layer | | |
|---|---|---|
| Emulsion A | silver | 0.20 g |
| Emulsion B | silver | 0.15 g |
| Emulsion C | silver | 0.08 g |
| 5th layer | | |
| Emulsion C | silver | 0.18 g |
| Emulsion D | silver | 0.21 g |
| 6th layer | | |
| Emulsion E | silver | 0.16 g |
| Emulsion F | silver | 0.16 g |

TABLE 3

Constitution of samples

| Sample | | Coupler in 4th, 5th and 6th layers | High-boiling organic solvent in 4th, 5th and 6th layers Kind | Amount (wt. ratio to coupler) |
|---|---|---|---|---|
| 101 | Comparison | As described in the text | | |
| 102 | Comparison | Comparative coupler (a) | Oil-2 | 1.0 |
| 103 | Comparison | Comparative coupler (b) | Oil-5 | 0.25 |
| 104 | Comparison | Comparative coupler (c) | Oil-5 | 0.25 |
| 105 | Invention | (1) | Oil-5 | 0.25 |
| 106 | Invention | (2) | Oil-5 | 0.25 |
| 107 | Invention | (2) | Oil-5/A (wt. ratio 8:2) | 0.25 |
| 108 | Invention | (3) | Oil-5 | 0.25 |
| 109 | Invention | (1) | Oil-A | 0.45 |
| 110 | Invention | (1) | Oil-A/B(4:1) | 0.45 |
| 111 | Invention | (1) | Oil-A/B(5:5) | 0.35 |

TABLE 3-continued

Constitution of samples

| Sample | | Coupler in 4th, 5th and 6th layers | High-boiling organic solvent in 4th, 5th and 6th layers | |
|---|---|---|---|---|
| | | | Kind | Amount (wt. ratio to coupler) |
| 112 | Invention | (15) | Oil-A | 0.45 |
| 113 | Invention | (7) | Oil-A | 0.45 |
| 114 | Invention | (2) | Oil-A | 0.3 |
| 115 | Invention | (2) | Oil-B | 0.3 |
| 116 | Invention | (2) | Oil-2 | 0.05 |
| 117 | Invention | (1) | none | none |
| 118 | Invention | (5) | Oil-A | 0.5 |
| 119 | Invention | (2) + CC-1(5 mol%) | Oil-A/B (wt. ratio 4:6) | 0.3 |

In this example, the following development processing steps (Development processing A) was performed.

On the occasion of the processing, the processing for the evaluation was performed after a running processing using Sample 101 of unexposed and that of full exposed in a ratio of 1:1, until the replenishing amount became 4 times the tank volume.

(Processing Steps)

| Processing Step | Time | Temperature | Tank volume | Replenishment rate |
|---|---|---|---|---|
| 1st development | 6 min | 38° C. | 195 L | 2,200 mL/m² |
| 1st washing | 2 min | 38° C. | 55 L | 4,000 mL/m² |
| Reversal | 2 min | 38° C. | 90 L | 1,100 mL/m² |
| Color development | 6 min | 38° C. | 180 L | 2,200 mL/m² |
| Pre-bleaching | 2 min | 38° C. | 70 L | 1,100 mL/m² |
| Bleaching | 6 min | 38° C. | 160 L | 220 mL/m² |
| Fixing | 4 min | 38° C. | 120 L | 1,100 mL/m² |
| 2nd washing | 4 min | 38° C. | 100 L | 4,000 mL/m² |
| Final rinsing | 1 min | 25° C. | 45 L | 1,100 mL/m² |

The compositions of the processing solutions were as follows.

| <1st developer> | <Tank solution> | <Replenisher> |
|---|---|---|
| Nitrilo-N,N,N-trimethylene phosphonic acid. pentasodium salt | 1.5 g | 1.5 g |
| Diethylenetriamine pentaacetic acid. pentasodium salt | 2.0 g | 2.0 g |
| Sodium sulfite | 30 g | 30 g |
| Hydroquinone.potassium monosulfonate | 20 g | 20 g |
| Potassium carbonate | 15 g | 20 g |
| Potassium bicarbonate | 12 g | 15 g |
| 1-phenyl-4-methyl-4-hydroxymethyl-3-pyrazolidone | 2.5 g | 3.0 g |
| Potassium bromide | 2.5 g | 1.4 g |
| Potassium thiocyanate | 1.2 g | 1.2 g |
| Potassium iodide | 2.0 mg | — |
| Diethyleneglycol | 13 g | 15 g |
| Water to make | 1,000 mL | 1,000 mL |
| pH | 9.60 | 9.60 |

The pH was adjusted by sulfuric acid or potassium hydroxide.

| <Reversal solution> | <Tank solution> | <Replenisher> |
|---|---|---|
| Nitrilo-N,N,N-trimethylene phosphonic acid. pentasodium salt | 3.0 g | 3.0 g |
| Stannous chloride.dihydrate | 1.0 g | 1.0 g |
| p-aminophenol | 0.1 g | 0.1 g |
| Sodium hydroxide | 8 g | 8 g |
| Glacial acetic acid | 15 mL | 15 mL |
| Water to make | 1,000 mL | 1,000 mL |
| pH | 6.00 | 6.0 |

The pH was adjusted by acetic acid or sodium hydroxide.

| <Color developer> | <Tank solution> | <Replenisher> |
|---|---|---|
| Nitrilo-N,N,N-trimethylene phosphonic acid· pentasodium salt | 2.0 g | 2.0 g |
| Sodium sulfite | 7.0 g | 7.0 g |
| Trisodium phosphate. dodecahydrate | 36 g | 36 g |
| Potassium bromide | 1.0 g | — |
| Potassium iodide | 90 mg | — |
| Sodium hydroxide | 12.0 g | 12.0 g |
| Citrazinic acid | 0.5 g | 0.5 g |
| N-ethyl-N-(β-methanesulfonamidoethyl)-3-methyl-4 aminoaniline.3/2 sulfuric acid·monohydrate | 10 g | 10 g |
| 3,6-dithiaoctane-1,8-diol | 1.0 g | 1.0 g |
| Water to make | 1,000 mL | 1,000 mL |
| pH | 11.80 | 12.00 |

The pH was adjusted by sulfuric acid or potassium hydroxide.

| <Pre-bleaching solution> | <Tank solution> | <Replenisher> |
|---|---|---|
| Ethylenediaminetetraacetic acid.disodium salt. dihydrate | 8.0 g | 8.0 g |
| Sodium sulfite | 6.0 g | 6.0 g |
| 1-thioglycerol | 0.4 g | 0.4 g |
| Formaldehyde sodium bisulfite adduct | 30 g | 35 g |
| Water to make | 1,000 mL | 1,000 mL |
| pH | 6.30 | 6.10 |

The pH was adjusted by acetic acid or sodium hydroxide.

| <Bleaching solution> | <Tank solution> | <Replenisher> |
|---|---|---|
| Ethylenediaminetetraacetic acid.disodium salt. dihydrate | 8.0 g | 8.0 g |
| Ethylenediaminetetraacetic acid.Fe(III).ammonium. dihydrate | 120 g | 240 g |
| Potassium bromide | 100 g | 200 g |
| Ammonium nitrate | 10 g | 20 g |
| Water to make | 1,000 mL | 1,000 mL |
| pH | 5.70 | 5.50 |

The pH was adjusted by nitric acid or sodium hydroxide.

| <Fixing solution> | <Tank solution> | <Replenisher> |
|---|---|---|
| Ammonium thiosulfate | 80 g | 80 g |
| Sodium sulfite | 5.0 g | 5.0 g |
| Sodium bisulfite | 5.0 g | 5.0 g |
| Water to make | 1,000 mL | 1,000 mL |
| pH | 6.60 | 6.60 |

The pH was adjusted by acetic acid or ammonia water.

| <Stabilizer> | <Tank solution> | <Replenisher> |
|---|---|---|
| 1,2-benzoisothiazoline-3-one | 0.02 g | 0.03 g |
| Polyoxyethylene-p-monononyl phenylether (average polymerization degree = 10) | 0.3 g | 0.3 g |
| Polymaleic acid (average molecular weight = 2,000) | 0.1 g | 0.15 g |
| Water to make | 1,000 mL | 1,000 mL |
| pH | 7.0 | 7.0 |

In the above described development processing steps, each bath was stirred by continuously circulating the solutions, and further, the bottom surface of each tank was provided with a bubbling tube having apertures of 0.3 mm diameter in an interval of 1 cm, by which nitrogen gas was continuously bubbled to sire the solutions.

(Estimation)

(Estimation of Dependence on Processing)

Development processing B comprised the same processing as the development processing A except that the replenisher volumes for reversal and color development were 250 mL and 800 mL, respectively. Running processing was carried out in the same manner as that of the development processing A, and thereafter, tests were performed.

Two sets were provided with respect to each of the samples 101 to 119, and exposed to white light through a wedge of continuous density change. One set was subjected to the development processing A while the other set was subjected to the development processing B.

Thereafter, density measurement was carried out. The difference of cyan density between development processing A and development processing B at a point for realizing a cyan density of 3.0 upon the development processing A was determined (development processing A realized higher value).

(Estimation of Image Storability)

The exposure was performed in the above manner, and the samples having undergone the development processing A were stored for 7 days under such conditions that the temperature was 30° C. and the humidity 100% RH. The densities of minimum density area immediately after the processing and also after the storage were measured, so that the increase of magenta density exhibited upon storage in high-humidity condition was studied. The less the density increase, the greater the preference.

The obtained results are listed in Table 4.

TABLE 4

| | | Evaluation results | |
|---|---|---|---|
| Sample | | Processing dependency Change in cyan density | Magenta dyeing of white background |
| 101 | Comparison | −0.20 | 0 |
| 102 | Comparison | −0.30 | +0.020 |
| 103 | Comparison | −0.32 | +0.025 |
| 104 | Comparison | −0.30 | +0.020 |
| 105 | Invention | −0.12 | 0 |
| 106 | Invention | −0.10 | 0 |
| 107 | Invention | −0.12 | 0 |
| 108 | Invention | −0.08 | 0 |
| 109 | Invention | −0.08 | 0 |
| 110 | Invention | −0.08 | 0 |
| 111 | Invention | −0.10 | 0 |
| 112 | Invention | −0.10 | 0 |
| 113 | Invention | −0.10 | 0 |
| 114 | Invention | −0.12 | 0 |
| 115 | Invention | −0.10 | 0 |
| 116 | Invention | −0.07 | 0 |
| 117 | Invention | −0.15 | 0 |
| 118 | Invention | −0.10 | 0 |
| 119 | Invention | −0.12 | 0 |

As apparent from Table 4, the comparative couplers A, B and C posed such a problem of processing dependence that the cyan maximum density was lowered when the replenishment rates of reversal bath and color development bath were reduced, and further posed such a problem that unfavorable magenta dyeing of white background occurred when the samples after processing were stored in high-humidity condition.

By contrast, the samples 105 to 119 of the present invention were favorably improved with respect to the dependence on processing and staining of white background.

Example-2

Samples 201 to 219 were prepared in the same manner as the samples 101 to 119 except that the compositions of the 9th, 10th and 11th layers were changed to those listed below and except that with respect to the additives of 14th, 15th and 16th layers, all the coating amounts were increased 1.15-fold without changing of the proportion thereof.

| 9th layer (Low-speed green-sensitive emulsion layer) | | |
|---|---|---|
| Emulsion G | silver | 0.20 g |
| Emulsion H | silver | 0.20 g |
| Emulsion I | silver | 0.20 g |
| Gelatin | | 1.70 g |
| Coupler MC-1 | | 0.20 g |
| Coupler MC-2 | | 0.060 g |
| Compound Cpd-R | | 0.020 g |
| Compound Cpd-B | | 0.030 g |
| Compound Cpd-D | | 5.0 mg |
| Compound Cpd-G | | 2.5 mg |
| Compound Cpd-F | | 0.010 g |
| Compound Cpd-K | | 2.0 mg |
| Ultraviolet absorber U-6 | | 5.0 mg |
| High-boiling organic solvent Oil-2 | | 0.050 g |
| 10th layer (Medium-speed green-sensitive emulsion layer) | | |
| Emulsion I | silver | 0.15 g |
| Emulsion J | silver | 0.20 g |

-continued

| | | |
|---|---|---|
| Gelatin | | 0.80 g |
| Coupler MC-1 | | 0.20 g |
| Coupler MC-2 | | 0.050 g |
| Compound Cpd-R | | 0.020 g |
| Compound Cpd-B | | 0.030 g |
| Compound Cpd-G | | 2.0 mg |
| High-boiling organic solvent Oil-2 | | 0.050 g |
| 11th layer (High-speed green-sensitive emulsion layer) | | |
| Emulsion K | silver | 0.45 g |
| Gelatin | | 1.00 g |
| Coupler MC-1 | | 0.30 g |
| Coupler MC-2 | | 0.070 g |
| Coupler C-7 | | 0.10 g |
| Compound Cpd-R | | 0.040 g |
| Compound Cpd-A | | 5.0 mg |
| Compound Cpd-B | | 0.030 g |
| High-boiling organic solvent Oil-2 | | 0.050 g |

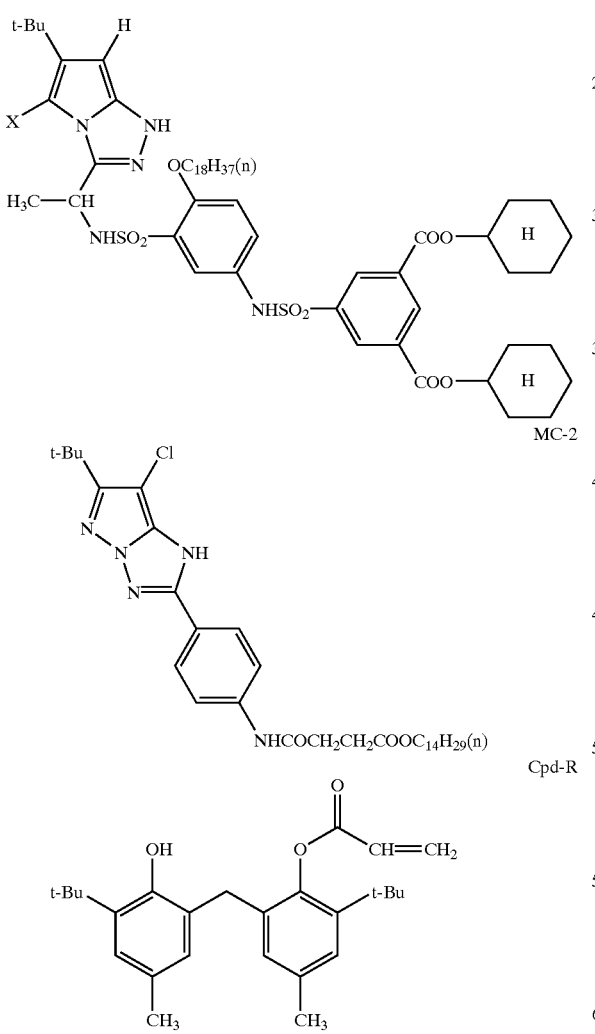

Samples 201 to 219 were estimated in the same manner as in Example-1. The samples of the present invention produced desirable results.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A silver halide color photosensitive material comprising at least one layer on a support, wherein at least one of the layers contains a compound represented by the following general formula (I):

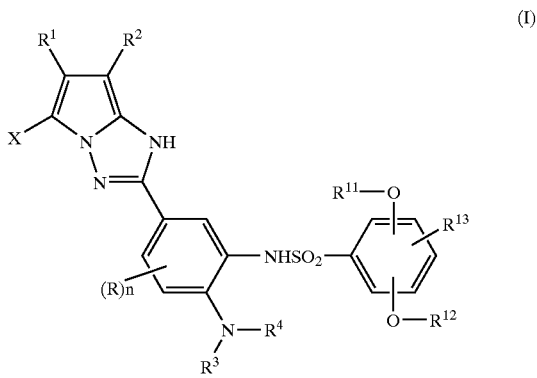

wherein X represents a hydrogen atom or a split-off group; each of $R^1$ and $R^2$ represents an electron withdrawing group whose Hammett substituent constant σp value is 0.20 or greater, provided that the sum of $R^1$ and $R^2$ σp values is 0.65 or greater; $R^3$ represents a substituted or unsubstituted alkyl group, substituted or unsubstituted alkenyl group, substituted or unsubstituted alkynyl group, substituted or unsubstituted cycloalkyl group, substituted or unsubstituted cycloalkenyl group, substituted or unsubstituted aryl group, or substituted or unsubstituted heterocyclic group; $R^4$ represents a hydrogen atom, a substituted or unsubstituted alkyl group, substituted or unsubstituted alkenyl group, substituted or unsubstituted alkynyl group, substituted or unsubstituted cycloalkyl group, substituted or unsubstituted cycloalkenyl group, substituted or unsubstituted aryl group, substituted or unsubstituted acyl group, substituted or unsubstituted alkoxycarbonyl group, substituted or unsubstituted aryloxycarbonyl group, or substituted or unsubstituted carbamoyl group, provided that $R^3$ and $R^4$ may be bonded with each other to thereby form a ring; each of $R^{11}$, $R^{12}$ and $R^{13}$ independently represents a linear, branched or cyclic alkyl group having 1 to 30 carbon atoms; R represents a substituent; and n represents an integer of 0 to 3.

2. A method of forming an image by using the silver halide color photosensitive material according to claim 1.

3. The silver halide color photosensitive material according to claim 1, wherein the silver halide color photosensitive material is a reversal photosensitive material.

4. A method of reducing a magenta stain of a silver halide color photosensitive material by using the silver halide color photosensitive material according to claim 1.

5. A silver halide color photosensitive material comprising at least one layer on a support, wherein at least one of the layers contains a compound represented by the following general formula (I):

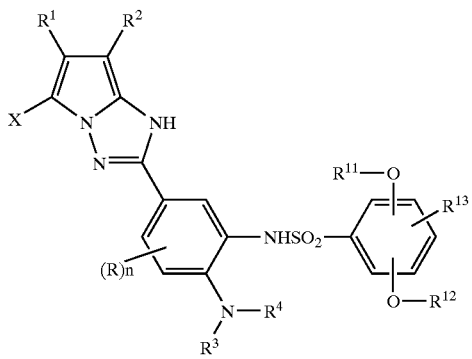

wherein X represents a hydrogen atom, halogen atom, alkoxy group having 1 to 32 carbon atoms, aryloxy group having 6 to 32 carbon atoms, alkylthio group having 1 to 32 carbon atoms, arylthio group having 6 to 32 carbon atoms, heterocyclic thio group having 2 to 32 carbon atoms, alkoxycarbonyloxy group having 2 to 32 carbon atoms, aryloxycarbonyloxy group having 7 to 32 carbon atoms, carbamoyloxy group having 1 to 32 carbon atoms, heterocyclic carbonyloxy group having 3 to 32 carbon atoms, or 5 or 6-membered nitrogen-containing heterocyclic group having 2 to 32 carbon atoms, the heterocyclic group bonding to the coupling active site with its nitrogen atom; $R^1$ represents a cyano group; $R^2$ represents an alkoxycarbonyl group; $R^3$ represents a substituted or unsubstituted alkyl group, substituted or unsubstituted alkenyl group, substituted or unsubstituted alkynyl group, substituted or unsubstituted cycloalkyl group, substituted or unsubstituted cycloalkenyl group, substituted or unsubstituted aryl group, or substituted or unsubstituted heterocyclic group; $R^4$ represents a hydrogen atom, substituted or unsubstituted alkyl group, substituted or unsubstituted alkenyl group, substituted or unsubstituted alkynyl group, substituted or unsubstituted cycloalkyl group, substituted or unsubstituted cycloalkenyl group, substituted or unsubstituted aryl group, substituted or unsubstituted acyl group, substituted or unsubstituted alkoxycarbonyl group, substituted or unsubstituted aryloxycarbonyl group, or substituted or unsubstituted carbamoyl group, provided that $R^3$ and $R^4$ may be bonded with each other to thereby form a ring; each of $R^{11}$, $R^{12}$ and $R^{13}$ independently represents a linear, branched or cyclic alkyl group having 1 to 30 carbon atoms; R represents a substituent; and n represents an integer of 0 to 3.

6. A method of forming an image by using the silver halide color photosensitive material according to claim 5.

7. The silver halide color photosensitive material according to claim 5, wherein the silver halide color photosensitive material is a reversal photosensitive material.

8. A method of reducing a magenta stain of a silver halide color photosensitive material by using the silver halide color photosensitive material according to claim 5.

* * * * *